(12) United States Patent  (10) Patent No.: US 6,809,200 B2
Allerton et al.  (45) Date of Patent: Oct. 26, 2004

(54) PROCESS FOR THE PREPARATION OF PYRAZOLO[4,3-D]PYRIMIDIN-7-ONE COMPOUNDS AND INTERMEDIATES THEREOF

(75) Inventors: Charlotte Moira Norfor Allerton, Kent (GB); Christopher Gordon Barber, Kent (GB); Keith Michael DeVries, Groton, CT (US); Laurence James Harris, Kent (GB); Philip Charles Levett, Kent (GB); Joanna Teresa Negri, Groton, CT (US); David James Rawson, Kent (GB); Albert Shaw Wood, Kent (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/916,099

(22) Filed: Jul. 26, 2001

(65) Prior Publication Data

US 2002/0038024 A1 Mar. 28, 2002

Related U.S. Application Data

(60) Provisional application No. 60/276,532, filed on Mar. 16, 2001, and provisional application No. 60/292,378, filed on May 21, 2001.

(30) Foreign Application Priority Data

| Jul. 28, 2000 | (GB) | ............................................ 0018660 |
| Mar. 26, 2001 | (GB) | ............................................ 0107526 |
| Apr. 26, 2001 | (GB) | ............................................ 0110251 |

(51) Int. Cl.[7] ...................... C07D 487/04; C07D 401/14
(52) U.S. Cl. .................................... 544/262; 546/275.4
(58) Field of Search ........................................ 544/262

(56) References Cited

U.S. PATENT DOCUMENTS

| 2,089,971 A | 8/1937 | Lesser |
| 6,251,904 B1 * | 6/2001 | Bunnage et al. ............. 544/262 |
| 6,350,751 B1 * | 2/2002 | Hughes et al. ............... 544/262 |
| 2003/0064990 A1 * | 4/2003 | Denton et al. ............... 544/262 |

FOREIGN PATENT DOCUMENTS

| EP | 0463756 | 1/1992 | ......... C07D/487/04 |
| EP | 1092720 | * 4/2001 | |
| WO | WO 9319059 | 9/1993 | ......... C07D/403/04 |
| WO | WO 0127112 | 4/2001 | ......... C07D/487/04 |

OTHER PUBLICATIONS

Berge et al., J. Pharm, Sci., 66, 1–19, 1977.
"Protecting Groups" edited by P. J. Kocienski, Thieme, NY 1994, chp. 4, pp. 118–154.

(List continued on next page.)

*Primary Examiner*—Mark L. Berch
(74) *Attorney, Agent, or Firm*—Peter C. Richardson; Gregg C. Benson; Martha G. Munchhof

(57) ABSTRACT

A process is provide for the preparation of compounds of formula (I) herein

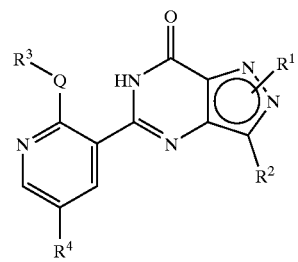

comprising reacting a compound of formula (III), (IV) or (V)

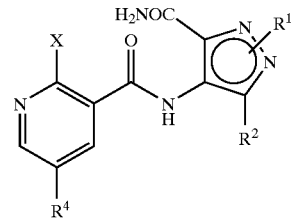

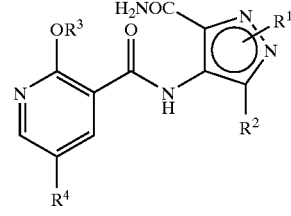

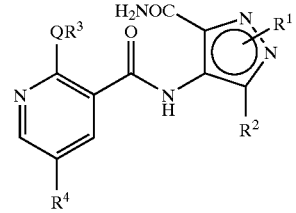

wherein the variables are as defined in the specification. The reaction is conducted in the presence of $^-OR^3$ and a hydroxide trapping agent or in the case of compounds of formula (IV) reacting in the presence of an auxiliary base and a hydroxide trapping agent.

3 Claims, No Drawings

OTHER PUBLICATIONS

"Protective Groups in Organic Synthesis", 2nd ed. T. W. Greene & PGM Wutz, Wiley–Interscience, 1991, chpt 5.

Terrett, N. K., et al., *Sildenafil (Viagra™), A Potent and Selective Inhibitor of Type 5 CGMP Phosphodiesterase with Utility for the Treatment of Male Erectile Dysfunction,* Biorganic & Medicinal Chemistry Letters; vol. 6, No. 15, pp. 1819–1824, 1996.

Dumaitre, et al., *Synthesis and Cyclic GMP Phosphodiesterase Inhibitory Activity of a Series of 6–phenylpyrazolo [3,4–d]pyrimidones,* J. Med. Chem., 39, pp. 1635–1644, 1996.

Ajello, T., *La trasformazione di alcuni isonitrosopirroli in derivati della pirimidina, la reazione di Ciamician e la constituzione dei nitrosopirroli e delle aldeidi pirrolche,* Gazzetta Chimica Italiano, vol. LXXII, pp. 325–333.

Hamilton, H. W., et al., *Syntesis and Structure–Activity Relationships of Pyrazolo[4,3–d]pyrimidin–7–ones as Adenosine Receptor Anatonists,* J. Med. Chem., vol. 30, pp. 91–96, 1987.

Billotte, S., et al, *Synthesis of C–Substituted Cyclic Amines Using Azacycloalkyl Organozinc Reagents,* Synlett, pp. 379–380, Apr. 1998.

Jung, M. E., et al., *New Synthesis of 2–Azetines and 1–Azabutadienes and the Use of the Latter in Diels–Alder Reactions: Total Synthesis of (±)–δ–Coniceine,* Journal of Organic Chemistry, vol. 56, No. 24, pp. 6729–2730, Nov. 22, 1991.

Anderson, A. G., Jr., et al., *The Synthesis of Azetidine–3–carboxylic Acid,* J. Org. Chem., vol. 37, No. 24, pp. 3953–3955, 1972.

\* cited by examiner

PROCESS FOR THE PREPARATION OF PYRAZOLO[4,3-D]PYRIMIDIN-7-ONE COMPOUNDS AND INTERMEDIATES THEREOF

This application is filed claiming priority from co-pending U.S. Provisional Application Nos. 60/276,532 filed Mar. 16, 2001 and 60/292,378 filed May 21, 2001.

This invention relates to a series of pyrazolo[4,3-d]pyrimidin-7-one compounds of formula I (as defined below) and intermediates thereof. More notably, most of the compounds of interest are inhibitors of type 5 cyclic guanosine 3',5'-monophosphate phosphodiesterase (CGMP PDE5) and have utility in a variety of therapeutic areas (such as male erectile dysfunction). A compound of particular interest is 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one (hereinafter compound of formula IA).

"Processes for the preparation of compounds of formula I are disclosed in WO 01/27112. In particular, example 132 of WO 01/27112 discloses a displacement reaction for preparing compound IA."

According to a first aspect of the invention there is provided a process for the preparation of a compound of formula (I):

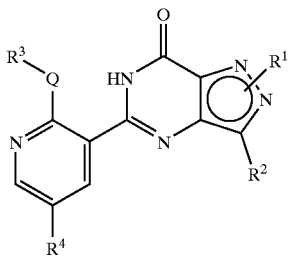

I or a pharmaceutically or veterinarily acceptable salt, prodrug, polymorph and/or solvate thereof, wherein Q represents O or $NR^5$ $R^1$ represents H, lower alkyl, Het, alkylHet, aryl or alkylaryl (which latter five groups are all optionally substituted and/or terminated with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

$R^2$ represents H, halo, cyano, nitro, $OR^6$, $OC(O)R^7$, $C(O)R^8$, $C(O)OR^9$, $C(O)NR^{10}R^{11}$, $NR^{12}R^{13}$, $SO_2NR^{14}R^{15}$, lower alkyl, Het, alkylHet, aryl or alkylaryl (which latter five groups are all optionally substituted and/or terminated with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

$R^3$ represents H, lower alkyl, alkylHet or alkylaryl (which latter three groups are all optionally substituted and/or terminated with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

$R^4$ represents H, halo, cyano, nitro, halo(loweralkyl), $OR^6$, $OC(O)R^7$, $C(O)R^8$, $C(O)OR^9$, $C(O)NR^{10}R^{11}$, $NR^{12}R^{13}$, $NR^{16}Y(O)R^{17}$, $N[Y(O)R^{17}]_2$, $SOR^{18}$, $SO_2R^{19}$, $C(O)AZ$, lower alkyl, lower alkenyl, lower alkynyl, Het, alkylHet, aryl, alkylaryl (which latter seven groups are all optionally substituted and/or terminated with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

Y represents C or S(O)

A represents lower alkylene

Z represents $OR^6$, halo, Het or aryl (which latter two groups are both optionally substituted with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

$R^{10}$ and $R^{11}$ independently represent H or lower alkyl (which latter group is optionally substituted and/or terminated with one or more substituents selected from halo, cyano, nitro, lower alkyl, halo(loweralkyl), $OR^6$, $OC(O)R^7$, $C(O)R^8$, $C(O)OR^9$, $C(O)NR^{10}R^{11}$, $NR^{12}R^{13}$, $SO_2NR^{14}R^{15}$ and $NR^{20}S(O)_2R^{21}$ or Het or aryl optionally substituted with one or more of said latter thirteen groups) or one of $R^{10}$ and $R^{11}$ may be lower alkoxy, amino or Het, which latter two groups are both optionally substituted with lower alkyl $R^{10a}$ and $R^{11a}$ independently represent $R^{10}$ and $R^{11}$ as defined above, except that they do not represent groups that include lower alkyl, Het or aryl, when these three groups are substituted and/or terminated (as appropriate) by one or more substituents that include one or more $C(O)NR^{10a}R^{11a}$ and/or $NR^{12}R^{13}$ groups $R^{12}$ and $R^{13}$ independently represent H or lower alkyl (which latter group is optionally substituted and/or terminated with one or more substituents selected from $OR^6$, $C(O)OR^9$, $C(O)NR^{22}R^{23}$ and $NR^{24}R^{25}$), one of $R^{12}$ or $R^{13}$ may be $C(O)$-lower alkyl or $C(O)$Het (in which Het is optionally substituted with lower alkyl), or $R^{12}$ and $R^{13}$ together represent $C_{3-7}$ alkylene (which alkylene group is optionally unsaturated, optionally substituted by one or more lower alkyl groups and/or optionally interrupted by O or $NR^{26}$)

$R^{14}$ and $R^{15}$ independently represent H or lower alkyl or $R^{14}$ and $R^{15}$, together with the nitrogen atom to which they are bound, form a heterocyclic ring $R^{16}$ and $R^{17}$ independently represent H or lower alkyl (which latter group is optionally substituted and/or terminated with one or more substituents selected from $OR^6$, $C(O)OR^9$, $C(O)NR^{22}R^{23}$ and $NR^{24}R^{25}$) or one of $R^{16}$ and $R^{17}$ may be Het or aryl, which latter two groups are both optionally substituted with lower alkyl $R^5$, $R^6$, $R^7$, $R^8$, $R^9$, $R^{18}$, $R^{19}$, $R^{20}$, $R^{22}$, $R^{23}$, $R^{24}$ and $R^{25}$ independently represent H or lower alkyl $R^{18}$ and $R^{19}$ independently represent lower alkyl $R^{21}$ represents lower alkyl or aryl $R^{28}$ represents H, lower alkyl, aryl, $C(O)R^{27}$ or $S(O)_2R^{28}$ $R^{27}$ represents H, lower alkyl or aryl $R^{28}$ represents lower alkyl or aryl Het represents an optionally substituted four- to twelve-membered heterocyclic group, which group contains one or more heteroatoms selected from nitrogen, oxygen, sulphur and mixtures thereof said process comprising reacting a compound of formula (II), (III), (IV) or (V) in the presence of $^-OR^3$ and a hydroxide trapping agent or, alternatively, in the case of compounds of formulae (IV) or (V) reacting in the presence of an auxiliary base and a hydroxide trapping agent. An auxiliary base as defined herein means a base other than $^-OR^3$ which is used in place of $^-OR^3$.

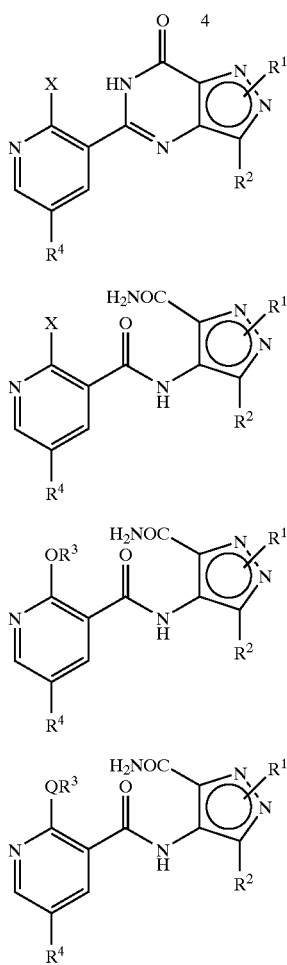

wherein X is a leaving group and Q and $R^1$ to $R^4$ are as defined above.

The term "aryl", when used herein, includes six- to ten-membered carbocyclic aromatic groups, such as phenyl and naphthyl, which groups are optionally substituted with one or more substituents selected from aryl (which group may not be substituted by any further aryl groups), lower alkyl, Het, halo, cyano, nitro, $OR^6$, $OC(O)OR^7$, $C(O)OR^8$, $C(O)OR^9$, $C(O)NR^{10a}R^{11a}$, $NR^{12a}R^{13a}$ (wherein $R^{12a}$ and $R^{13a}$ independently represent $R^{12}$ and $R^{13}$ as hereinbefore defined, except that: (i) they do is not represent C(O)Het in which Het is substituted by one or more substituents that include one or more $C(O)NR^{10a}R^{11a}$ and/or $NR^{12a}R^{13a}$, groups; or (ii) they do not together represent $C_{3-7}$ alkylene interrupted by $NR^{26}$) and $SO_2NR^{14}R^{15}$.

The term "Het", when used herein, includes four- to twelve-membered, preferably four- to ten-membered, ring systems, which rings contain one or more heteroatoms selected from nitrogen, oxygen, sulfur and mixtures thereof, and which rings may contain one or more double bonds or be non-aromatic, partly aromatic or wholly aromatic in character. The ring systems may be monocyclic, bicyclic or fused. Each "Het" group identified herein is optionally substituted by one or more substituents selected from halo, cyano, nitro, oxo, lower alkyl (which alkyl group may itself be optionally substituted or terminated as defined below), $OR^6$, $OC(O)R^7$, $C(O)R^8$, $C(O)OR^9$, $C(O)NR^{10a}R^{11a}$, $NR^{12a}R^{13a}$ and $SO_2NR^{14}R^{15}$. The term thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, tetrazolyl, oxatriazolyl, thiatriazolyl, pyridazinyl, morpholinyl, pyrimidinyl, pyrazinyl, pyridinyl, quinolinyl, isoquinolinyl, piperidinyl, pyrazolyl imidazopyridinyl and piperazinyl. Substitution at Het may be at a carbon atom of the Het ring or, where appropriate, at one or more of the heteroatoms.

"Het" groups may also be in the form of an N-oxide.

The heterocyclic ring that $R^{14}$ and $R^{15}$ (together with the nitrogen atom to which they are bound) may represent may be any heterocyclic ring that contains at least one nitrogen atom, and which ring forms a stable structure when attached to the remainder of the molecule via the essential nitrogen atom (which, for the avoidance of doubt, is the atom to which $R^{14}$ and $R^{15}$ are attached). In this respect, heterocyclic rings that $R^{14}$ and $R^{15}$ (together with the nitrogen atom to which they are bound) may represent include four- to twelve-membered, preferably four- to ten-membered, ring systems, which rings contain at least one nitrogen atom and optionally contain one or more further heteroatoms selected from nitrogen, oxygen and/or sulfur, and which rings may contain one or more double bonds or be non-aromatic, partly aromatic or wholly aromatic in character. The term thus includes groups such as azetidinyl, pyrrolidinyl, imidazolyl, indolyl, isoazoyl, oxazoyl, triazolyl, tetrazolyl, morpholinyl, piperidinyl, pyrazolyl and piperazinyl.

The term "lower alkyl" (which includes the alkyl part of alkylHet and alkylaryl groups), when used herein, means $C_{1-6}$ alkyl and includes methyl, ethyl, propyl, butyl, pentyl and hexyl groups. Unless otherwise specified, alkyl groups may, when there is a sufficient number of carbon atoms, be linear or branched, be saturated or unsaturated, be cyclic, acyclic or part cyclic/acyclic, and/or be substituted by one or more halo atoms. Preferred lower alkyl groups for use herein are $C_{1-3}$ alkyl groups. Alkyl groups which $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ may represent, and with which $R^1$, $R^2$, $R^3$, $R^4$, $R^{10}$, $R^{11}$, $R^{12}$, $R^{13}$, $R^{16}$, $R^{17}$, aryl, alkylaryl, alkylHet and Het may be substituted, may, when there is a sufficient number of carbon atoms, be linear or branched, be saturated or unsaturated, be cyclic, acyclic or part cyclic/acyclic, be interrupted by one or more of oxygen, sulfur and optionally alkylated or optionally acylated nitrogen and/or be substituted by one or more halo atom. The terms "lower alkenyl" and "lower alkynyl", when used herein, include $C_{2-6}$ groups having one or more double or triple carbon-carbon bonds, respectively. Otherwise, the terms "lower alkenyl" and "lower alkynyl" are defined in the same way as the term "lower alkyl". Similarly, the term "lower alkylene", when used herein, includes $C_{1-6}$ groups which can be bonded at two places on the group and is otherwise defined in the same way as "lower alkyl". The term "acyl" includes C(O)-lower alkyl.

In the above definition, unless otherwise indicated, alkyl, alkoxy and alkenyl groups having three or more carbon atoms, and alkanoyl groups having four or more carbon atoms, may be straight chain or branched chain.

The terms "alkylHet" and "alkylaryl" include $C_{1-6}$ alkylHet and $C_{1-6}$ alkylaryl. The alkyl groups (e.g. the $C_{1-6}$ alkyl groups) of alkylHet and alkylaryl may, when there is a sufficient number of carbon atoms, be linear or branched, be saturated or unsaturated, and/or be interrupted by oxygen. When used in this context, the terms "Het" and "aryl" are as defined hereinbefore. Substituted alkylHet and alkylaryl may have substituents on the ring and/or on the alkyl chain.

Halo groups with which the above-mentioned groups may be substituted or terminated include fluoro, chloro, bromo and iodo and the terms haloalkyl and haloalkoxy include CF₃ and OCF₃ respectively.

Compounds of general formula (I) can be represented by formulae I' and I'':

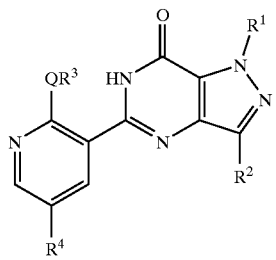

(I')

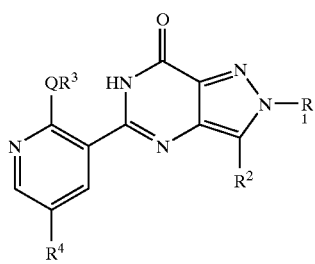

(I'')

wherein R¹, R², R³, R⁴ and Q are as defined hereinbefore.

The compounds of formulae (I) may contain one or more chiral centres and therefore can exist as stereoisomers, i.e. as enantiomers or diastereoisomers, as well as mixtures thereof. The invention relates to formation of both the individual stereoisomers of the compounds of formulae (I) and any mixture thereof.

In a first preferred embodiment of the invention a compound of formulae (IA) is prepared.

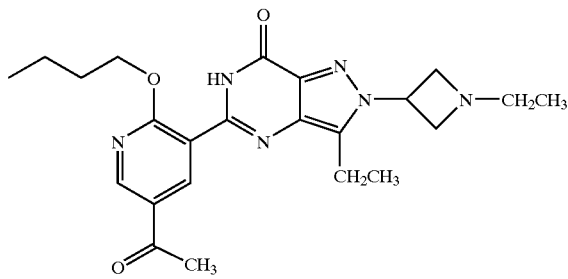

(IA)

Accordingly, in a preferred aspect of the invention there is provided a process for the preparation of a compound of formula (IA).

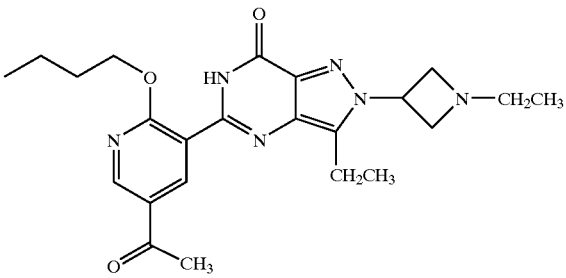

(IA)

comprising reacting a compound of formula (IIA), (IIIA) or (IVA) respectively

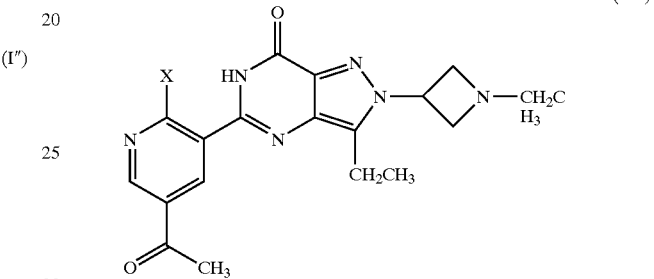

(IIA)

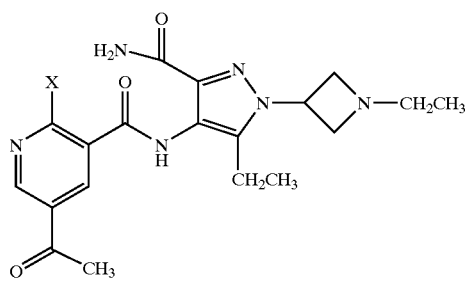

(IIIA)

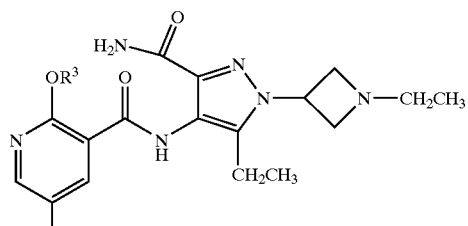

(IVA)

in the presence of ⁻OR³ and a hydroxide trapping agent, or alternatively in the case of compounds of formula (IVA) reacting in the presence of a hydroxide trapping agent and an auxiliary base, wherein OR³ in the case of formation of compound (IA) and (IVA) is CH₃(CH₂)₃O— and wherein X in formulae (IIA) and (IIIA) is a leaving group.

Intermediates of the general formula (IIA), (IIIA) and (IVA), where novel, form further aspects of the invention.

As a result of use of the hydroxide trapping agent, a particular advantage of the present process is that a high yield of final product (compounds of formula (I, IA) and intermediate compounds (II, IIA) can be obtained.

In a preferred embodiment compounds of formula (I) can be obtained in good yield without intermediate isolation.

It is most advantageous to form the compounds of formula (I) from intermediates of formula (III) since the cyclisation step (III to II) and the nucleophilic displacement of X by $^-OR^3$ (II to I) can be carried out in a one-pot reaction. Furthermore this process can be run at ambient pressure whereas the cyclisation step of the 2 step process can require higher pressures where XH is a lower alkanol, such as methanol, ethanol or isomers of propanol.

In a further aspect of the invention, there is provided a process for the formation of compounds of formula (II) (more particularly IIA wherein X in II/IIA=—$OR^3$) comprising the cyclisation of compounds of formula (III) (more particularly IIIA) wherein X is a leaving group as defined hereinbefore, in the presence of said hydroxide trapping agent. Again, this step benefits from the higher yield provided by using the hydroxide trapping agent.

Of course, the trapping agent technology could be used to form compounds of formula (IV) (more particularly IVA) from compounds of formula (III) (more particularly IIIA) in the presence of $^-OR^3$, advantageously up to about 1 molar equivalent of $^-OR^3$ (to compounds (III)). If substantially more than 1 equivalent of $^-OR^3$ was used, the reaction would proceed through to compounds (I) (more particularly IA).

Preferably the hydroxide trapping agent is an ester.

More preferably said hydroxide trapping agent is an ester of the formula:

TOC(O)W wherein OT is $OR^3$ as defined hereinbefore or, OT is the residue of a bulky alcohol or a non-nucleophilic alcohol, or TOH is an alcohol which can be azeotropically removed during the reaction;
and C(O)W is the residue of a carboxylic acid.

For example, where X is OEt in compound (IIA) and (IIIA) the ester trapping agent can be n-butyl acetate (i.e. OT=X and C(O)W is a residue of acetic acid), or ethyl acetate or ethyl pivalate, more preferably butyl pivalate (OT=X and C(O)W is the residue of pivalic acid- i.e. a carboxylic acid with no enolisable proton).

In a most preferred process, wherein X is OEt in compound (IIA) or (IIIA) the ester trapping agent is butyl actetate.

Preferably X is selected from the group consisting of optionally substituted arylsulphonyloxy, preferably phenylsulphonyloxy, more preferably a para substituted aryl (phenyl) such as by a $C_1$–$C_4$ alkyl group e.g. p-toluenesulphonyloxy; $C_1$–$C_4$ alkylsulphonyloxy e.g. methanesulphonyloxy; nitro or halo substituted benzenesulphonyloxy preferably para substituted e.g. p-bromobenzenesulfonyloxy or p-nitrobenzenesulphonyloxy; $C_1$–$C_4$ perfluoroalkylsulphonyloxy e.g. trifluoromethylsulphonyloxy; optionally substituted aroyloxy such as benzoyloxy; $C_1$–$C_4$ perfluoroalkanoyloxy such as trifluoroacetyloxy; $C_1$–$C_4$ alkanoyloxy such as acetyloxy; halo; diazonium; $C_1$–$C_6$ primary and secondary alkoxy such as methoxy; quatenaryammonium $C_1$–$C_4$ alkylsulphonyloxy; halosulphonyloxy e.g. fluorosulphonyloxy and other fluorinated leaving groups; and diarylsulphonylamino e.g. ditosyl ($NTs_2$).

Most preferably, for formation of compounds of formula (I) more particularly (IA), X is a $C_1$–$C_4$ alkoxy (advantageously ethoxy or methoxy) or halogen since this lends itself to simpler and cheaper formation of compounds—for example see Schemes 1 and 3 hereinafter.

An advantage of using labile leaving groups such as chloro or fluoro may be that an inert solvent could then be used rather than $R^3OH$ (which will often be more expensive). Thus only a sufficient amount of $OR^3$ (such as from $R^3OH$) as reactant would be required.

— $^-OR^3$ can act both as a nucleophile (to displace the leaving group by nucleophilic substitution) and as a base (to bring about the cyclisation).

— $^-OR^3$ can be generated in solution from, for example, a salt $ZOR^3$ (wherein Z is a cation) such as a metal salt. More particularly an alkali (such as sodium or potassium) or alkaline earth metal salt of —$^-OR^3$ in a suitable solvent would give rise to —$^-OR^3$ in solution. For example, potassium butoxide, potassium amylate, KHMDS or NaHMDS in a suitable solvent, under suitable temperature conditions, such as 1-butanol, with intermediate (IIA) or (IIIA) would form compound (IA). In another embodiment, —$^-OR^3$ can be formed in situ from $R^3OH$ plus an auxiliary base (i.e. a base other than $^-OR^3$). However, in another system, $ZOR^3$ could be used in the reaction system with an auxiliary base.

As will be appreciated the solvent in which the reaction takes place can be $R^3OH$ or an inert solvent (or a mixture of both). By inert solvent we mean a solvent which will not form a nucleophile under the reaction conditions, or, if a nucleophile is formed it is sufficiently hindered or un-reactive such that it does not substantially compete in the displacement reaction. When $R^3OH$ is used as a source of $^-OR^3$, then a separate solvent is not essentially required but an (auxiliary) inert solvent (i.e. a solvent other than $R^3OH$) may be used as a co-solvent in the reaction.

Suitable solvents are as follows:

$R^3OH$, a secondary or tertiary $C_4$–$C_{12}$ alkanol, a $C_3$–$C_{12}$ cycloalkanol, a tertiary $C_4$–$C_{12}$ cycloalkanol, a secondary or tertiary ($C_3$–$C_7$ cycloalkyl)$C_2$–$C_6$ alkanol, a $C_3$–$C_9$ alkanone, 1,2-dimethoxyethane, 1,2-diethoxyethane, diglyme, tetrahydrofuran, 1,4-dioxan, toluene, xylene, chlorobenzene, 1,2-dichlorobenzene, acetonitrile, dimethyl sulphoxide, sulpholane, dimethylformamide, N-methylpyrrolidin-2-one, pyridine, and mixtures thereof.

More preferably, the solvent is $R^3OH$, a tertiary $C_4$–$C_{12}$ alkanol, a tertiary $C_4$–$C_{12}$ cycloalkanol, a tertiary ($C_3$–$C_7$ cycloalkyl)$C_2$–$C_6$ alkanol, a $C_3$–$C_9$ alkanone, 1,2-dimethoxyethane, 1,2-diethoxyethane, diglyme, tetrahydrofuran, 1,4-dioxan, toluene, xylene, chlorobenzene, 1,2-dichlorobenzene, acetonitrile, dimethyl sulphoxide, sulpholane, dimethylformamide, N-methylpyrrolidin-2-one, pyridine, and mixtures thereof.

Most preferably the solvent is $R^3OH$, which means that $^-OR^3$ is formed in situ, such as, in the presence of an auxiliary base. For compound (IA) the solvent is preferably $CH_3(CH_2)_3OH$ (1-butanol).

A wide range of auxiliary bases can be used in the process of the invention. Typically the bases would not substantially compete with —$^-OR^3$ in the nucleophilic substitution of X (i.e. they would be non nucleophilic) such as by being suitably sterically hindered.

Preferably the auxiliary base is selected from the group consisting of a sterically hindered metal alkoxide base, a metal amide, a metal hydride, metal oxide, metal carbonate and metal bicarbonate.

Examples of suitable alcohol and amine metal salts include metal salts of: a secondary or tertiary $C_4$–$C_{12}$ alkanol; a $C_3$–$C_{12}$ cycloalkanol and a secondary or teritary ($C_3$–$C_8$ cycloalkyl)$C_1$–$C_6$ alkanol; a N-(secondary or tertiary $C_3$–$C_6$ alkyl)-N-(primary, secondary or tertiary $C_3$–$C_6$ alkyl)amine; a N-($C_3$–$C_8$ cycloalkyl)-N-(primary, secondary or tertiary $C_3$–$C_6$ alkyl)amine; a di($C_3$–$C_8$ cycloalkyl)amine or hexamethyldisilazane; or 1,5-diazabicyclo[4,3,0]non-5-ene and 1,8-diazabicyclo[5,4,0]undec-7-ene.

Examples of suitable metal salts of a tertiary $C_4$–$C_6$ alcohol such as the alkali or alkaline earth metal salts (e.g. Na/K) of t-butanol or t-amyl alcohol, or the base are: potassium t-butoxide, potassium hexamethyldisilazone (KHMDS) or NaHMDS.

More preferably the auxiliary base is a sterically hindered base selected from: metal salts of sterically hindered alcohols or amines; or metal carbonates. Preferred herein are metal carbonates, and advantageously potassium carbonate for the delivery of higher yield, improved impurity profile.

Further examples of suitable carbonate bases for use herein include sodium carbonate, caesium carbonate, lithium carbonate, rubidium carbonate, strontium carbonate, barium carbonate, beryllium carbonate and magnesium carbonate. Preferred for use herein are non-toxic carbonate bases with reasonably rapid reaction rate, in the cyclisation reaction according to the present invention. Potassium carbonate is especially preferred as defined hereinbefore.

Preferably the metal of the salt of $ZOR^3$ and the auxiliary base are independently selected from alkali metals (lithium, sodium, potassium, rubidium, caesium) or alkaline earth metals (beryllium, magnesium, calcium, strontium, barium). More preferably the metal is sodium or potassium and potassium is especially preferred.

To maximise yields, it is further preferred that at least about 1 molecular equivalent of auxiliary base and —$OR^3$ are used in accordance with the invention. If —$OR^3$ also functions as a base (i.e. there is no auxiliary base present) then preferably at least about 2 equivalents of $^-OR^3$ are present. Suitably, at least about 1 equivalent of trapping agent (preferably at least about 2 equivalents) is present. Especially preferred for use herein is about 3 equivalents of auxiliary base (preferably potassium carbonate) and at least about 1, preferably at least about 2 and especially about 3 equivalents of trapping agent (preferably butyl acetate).

The temperature of the cyclisation reaction of compounds (III) and (IV) to (I) (such as for the corresponding formation of compound (IA)) is preferably at least about 80° C., more preferably about 80 to about 130° C., more preferably still about 100 to about 130° C. and most preferably about 112° C. to about 122° C. These temperatures are also applicable for the conversion of compounds (II) to (I), although the temperature in this case could also probably be lower (e.g. about 60° C.) since there is no cyclisation taking place.

The reaction temperature attainable to effect the conversion of compounds of formulae (II) and (III) to compounds of formula (I) depends on the solvent, the nature of $^-OR^3$ and X. When X is an alkoxy and $R^3OH$ is the solvent, preferably XH (such as $C_{1-6}$ alkoxy) is removed azeotropically (of course the reaction vessel must be configured to distil over the azeotrope mixture) with $R^3OH$ by running the reaction at the azeotrope temperature of XH and $R^3OH$. In this way the yield and quality of the final product can be further improved. For example, (where X is an alkoxy) the conversion of compound (IIA), (IIIA) or (IVA) to (IA) is preferably carried out at the azeotrope temperature of the alcohol i.e. XH (preferably methanol or ethanol, most preferably ethanol) and 1-butanol.

Thus according to further preferred embodiments the invention provides:

A process for the synthesis of compound (IA) by reaction of compound (IIA) or (IIIA):

a) with 1-butanol and auxiliary base, preferably potassium butoxide, optionally in an inert solvent such as toluene and in the presence of said trapping agent TOC(O)W; or b) with $ZO(CH_2)_3CH_3$ and an auxiliary base in n-butanol or an inert solvent or both, in the presence of said trapping agent; or c) with $ZO(CH_2)_3CH_3$ and n-butanol or an inert solvent or both, in the presence of said trapping agent.

Preferably, the trapping agent is BuOC(O)W or $CH_3OC(O)W$ wherein C(O)W is a residue of a carboxylic acid (preferably sterically hindered) such as $CH_3(CH_2)_3OC(O)CH_3$ or $CH_3(CH_2)_3OC(O)(CH_3)_3$.

To maximise yields, it is further preferred that at least about 1 molecular equivalent of auxiliary base and —$OR^3$ are used in accordance with the invention. If —$OR^3$ also functions as a base (i.e. there is no auxiliary base present) then preferably at least about 2 equivalents of $^-OR^3$ are present. Thus to maximise yields of compounds (IA), suitably at least about 1 equivalent of trapping agent (preferably at least about 2 equivalents) is present. With respect to (a) above, preferably there is at least about 2 molecular equivalents of base and at least about 1 molecular equivalent of trapping agent relative to the substrate (more preferably at least about 2.2 and 2.5 respectively). For (b) above, preferably there is at least about 1 molecular equivalent of auxiliary base, trapping agent and $ZO(CH_2)CH_3$ relative to the substrate (more preferably at least about 1.2 equivalents of auxiliary base and at least about 2.5 equivalents of trapping agent). For (c) above, preferably there is at least about 2 molecular equivalents of $ZO(CH_2)_3CH_3$ and at least about 1 equivalent of trapping agent relative to the substrate (more preferably at least about 2 and 2.5 equivalents respectively).

To further improve yields of final product and reduce impurities, preferably C(O)W is the residue of a sterically hindered carboxylic acid and/or a carboxylic acid which does not contain an enolisable proton (e.g. pivalic acid).

The compounds of general formula (III) and (IIIA) may be obtained from readily available starting materials for example, by the routes depicted in the following reaction schemes. Reaction Scheme 1 illustrates for preparation of compounds of compounds of general formula (I) from compounds of formulae (IX) and (XII).

Compound (III) is formed by reaction of intermediate (IX) and compound (XII) in the presence of a coupling agent, such as N,N'-carbonyldiimidazole and a suitable solvent, such as ethyl acetate.

SCHEME 1

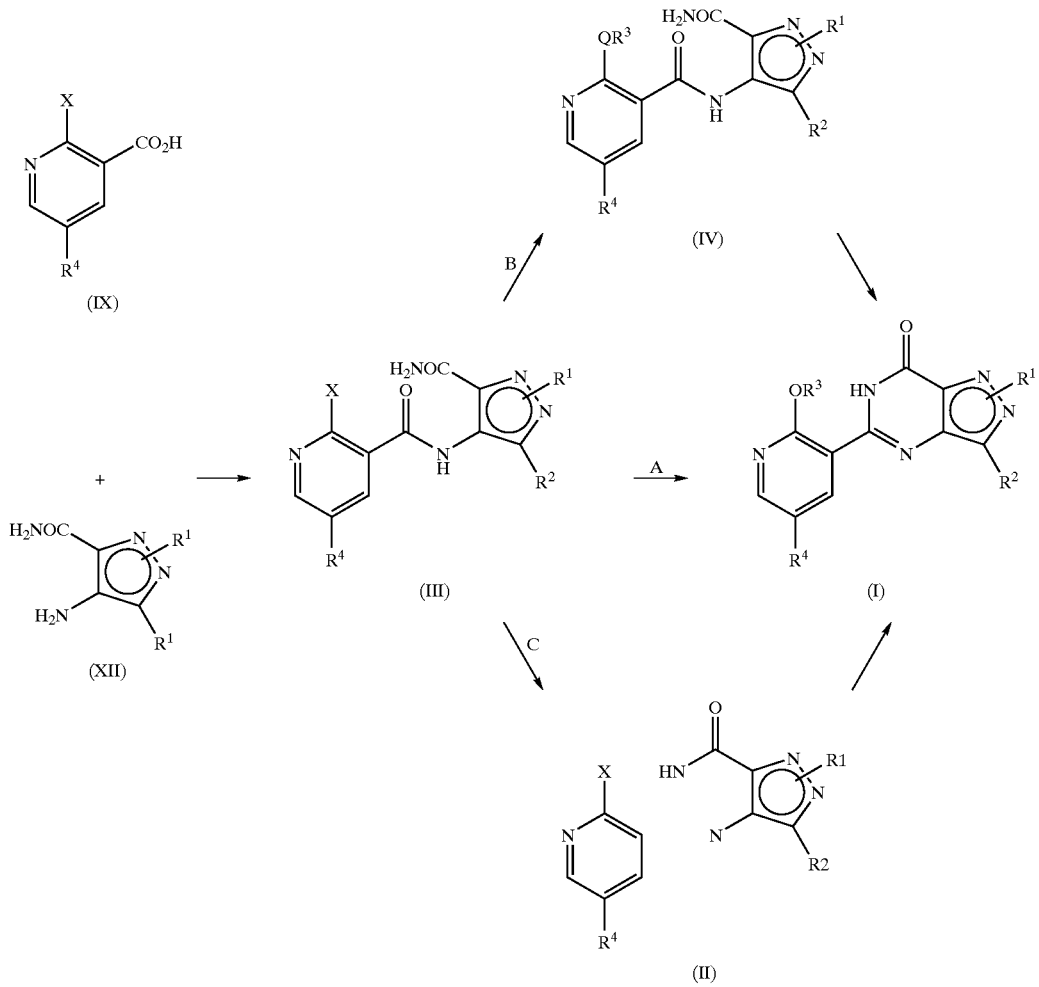

wherein $R^1$, $R^2$, $R^3$, $R^4$, X and Q are as defined hereinbefore.

Further suitable conditions for the coupling of compounds of formulae (XII) and (IX) to provide compounds of formula (III) include: conventional amide bond-forming techniques, e.g. via the acyl chloride derivative of (IX) in the presence of up to about a five-fold excess of a tertiary amine such as triethylamine or pyridine to act as scavenger for the acid by-product (e.g. HCl), optionally in the presence of a catalyst such as 4-dimethylaminopyridine, in a suitable solvent such as dichloromethane, at from about 0° C. to about room temperature. For convenience pyridine may also be used as the solvent.

In particular, any one of a host of amino acid coupling variations may be used. For example, the acid of formula (IX) or a suitable salt (e.g. sodium salt) thereof may be activated using a carbodiimide such as 1,3-dicyclohexylcarbodiimide or 1-ethyl-3-(3-dimethylaminoprop-1-yl)carbodiimide optionally in the presence of 1-hydroxybenzotriazole hydrate and/or a catalyst such as 4-dimethylaminopyridine, or by using a halotrisaminophosphonium salt such as for example bromotris(pyrrolidino)phosphonium hexafluorophosphate or by using a suitable pyridinium salt such as 2-chloro-1-methylpyridinium iodide. Either type of coupling is conducted in a suitable solvent such as dichloromethane, tetrahydrofuran or N,N-dimethylformamide, optionally in the presence of a tertiary amine such as triethylamine or N-ethyldiisopropylamine (for example when either the compound of formula (XII), or the activating reagent—for the acid of formula (IX), is presented in the form of an acid addition salt), at from about 0° C. to about room temperature. Preferably, from 1 to 2 molecular equivalents of the activating reagent and from 1 to 3 molecular equivalents of any tertiary amine present are employed.

In a further variation, the carboxylic acid function of acid (IX) may first of all be activated using up to about a 5% excess of a reagent such as N,N'-carbonyldiimidazole in a suitable solvent, e.g. ethyl acetate or butan-2-one, at from about room temperature to about 80° C., followed by reaction of the intermediate imidazolide with (XII) at from about 20° C. to about 90° C.

It will be appreciated that the general formula (XII) can also be represented by the regioisomeric formulae (XII') and (XII''):

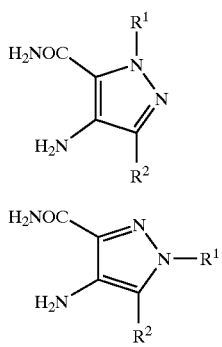

(XII')

(XII")

wherein $R^1$ and $R^2$ are as previously defined herein.

In Scheme 1 the compounds of general formula (I) can be prepared from compounds of general formula (III) by: cyclisation directly to a compound of formula (I), route A; exchange of "X" for "QR³ followed by cyclisation of compound (IV) to a compound of formula (I), route B; or by cyclisation to form a compound (II) followed by exchange of "X" for "OR³", route C. The cyclisation of route A includes both cyclisation where X=OR³ as well as cyclisation with alkoxide exchange where X is exchanged for OR³. Routes A, B and C are in a preferred process according to the present invention carried out in a one-pot process without isolation of intermediate compounds, such as for example compounds (II) or (IV).

Reaction Scheme 2 illustrates the preparation of compounds of general formula (IX) starting from the commercially available material, 2-hydroxynicotinic acid.

ethyl or methyl esters; aryl groups such as benzyl; or a silicon protecting group such as a trimethylsilyl (TMS) group.

As illustrated in Scheme 2, where not commercially available, the intermediate of formula (V) can be formed from commercially available starting materials such as 2-chloronicotinic acid or 2-hydroxynicotinic acid or a salt thereof by routine synthetic methods such as are exemplified hereinafter in the preparations section.

Intermediate compounds of formula (IX) wherein X=OR³ᵃ wherein OR³ᵃ is a different alkoxy group from OR³ wherein R³ᵃ is a $C_1-C_6$ alkyl group, preferably a $C_1-C_4$ alkyl group and $R^4$ is as defined hereinbefore can be formed from compounds of formula (VIII) (wherein X=OR³ᵃ and $R^4$ are as defined for (IX) and V is as defined hereinbefore) by hydrolysis, when V is an alkyl or aryl group, (IX) is preferably formed via base hydrolysis with metal hydroxide, more preferably with sodium hydroxide. Where V is a benzyl or silyl group, (IX) is formed via hydrogenation.

Compounds of formula (VIII) wherein X=OR³ᵃ and $R^4$ and V are as defined herein before, can be formed from compounds of formula (VII) (wherein X=OR³ᵃ and V are as defined for (VII) and P is as defined hereinbefore) via a substitution reaction (wherein group P is exchanged for the desired $R^4$ moiety), and preferably wherein such substitution reaction is a metal-mediated reaction. According to a preferred process said conversion is affected via acylation under Heck conditions as exemplified hereinafter.

Accordingly the present invention provides a process for the conversion of compound (VII) (wherein P=Br or 1, wherein X=OEt and wherein V is as defined hereinbefore) to compound (VIII) (wherein $R^4$=C(O)CH₃ and X=OEt and V is as defined hereinbefore) such as via reaction with butylvi-

SCHEME 2

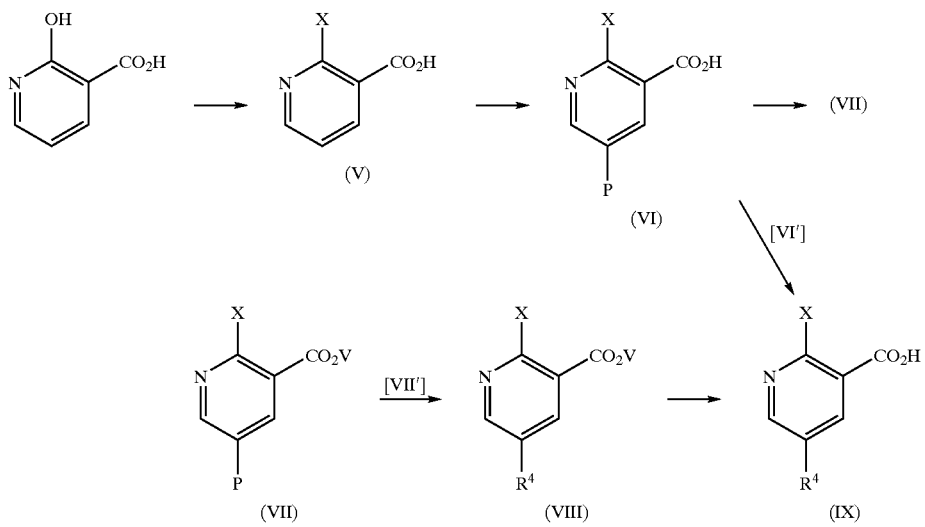

In the compounds of Scheme 2, X and $R^4$ are as hereinbefore defined. P is a group which can undergo an oxidative addition reaction with Palladium (0), such as for example halogen, trifluoromethanesulfonate, perfluoroethane sulfonate, diazonium salts and is preferably F, Cl, Br or I, more preferably Br or I. V is any suitable carboxylic acid protecting group such as: $C_1-C_4$ alkyl esters, preferably nyl ether and triethylamine in a suitable solvent, such as for example acetonitrile, dimethyl formamide (DMF), dimethyl acetamide (DMAC), N-methyl pyrrolidone (NMP) or water, under reflux conditions and at atmospheric pressure wherein said reaction is carried out in the presence of a suitable catalyst such as palladium acetate and a ligand such as tri-o-tolyl phosphine wherein the ratio of compound (VII) to acylating agent is about 1:15, preferably about 1:8, more preferably about 1:10 molecular equivalents and wherein the ratio of compound (VII) to base is about 1:2.0, preferably about 1:1.5 molecular equivalents and wherein the ratio of compound (VII) to catalyst in about 1:0.25, preferably about 1:0.16 molecular equivalents. To ensure appropriate conversion of the non-isolated intermediate enol-ether compound VIII' to the desired ester VIII the reaction should have an aqueous acidic work-up.

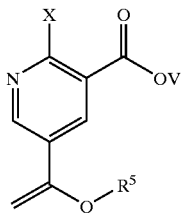

VIII' wherein X and V are as defined hereinbefore and wherein $R^5$ is a $C_1$–$C_5$ alkyl group, preferably $C_1$–$C_4$ alkyl and especially butyl.

Compounds of formula (VII) wherein X $OR^{3a}$ and V and P are as defined hereinbefore, and preferably wherein X=($C_1$–$C_4$) primary or secondary alkoxy and P is a halogen, can be formed from compounds of formula (VI) (wherein X and P are as defined for (VII)) in an esterification/protection reaction via treatment with a suitable acid catalyst and an alcohol of formula V—OH, or treatment with a suitable base and an alkylating agent wherein V is as defined hereinbefore, and wherein V is preferably $C_1$–$C_4$ alkyl. Preferred conditions wherein X=OEt; V—OH=$CH_3$—OH include: treatment with an HCl/$H_2SO_4$ mixture; or treatment with $H_2SO_4$; or treatment with ethyl iodide and cesium cabonate.

Compounds of formula (VI) (wherein X=$OR^{3a}$ and P is as previously defined) can be formed from compounds of formula (V) wherein X=$OR^{3a}$, via a halogenation reaction such as bromination with a suitable electrophilic halogenation agent i.e. N-bromosuccinamide.

It is possible to undertake the three step conversion of (VI) to (IX) (more particularly (VIA) to (IXA), see Scheme 5 hereinafter) in a single step.

Thus according to a highly preferred process of the invention and as illustrated in Scheme 2, compounds of general formula (VI) can be transformed directly into compounds of general formula (IX). Such direct transformation reactions proceed via a non isolated intermediate compound of general formula VI' as illustrated below:

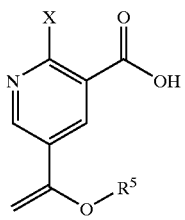

VI' wherein X is as defined herein before.

In such a highly preferred process compounds of formula (IX) can be prepared directly from compounds of formula (VI) in a one-step reaction. Suitable reagents for such direct conversion of compounds of formula (VI) to compounds of formula (IX) wherein X=$OR^{3a}$, preferably wherein X=OEt, and wherein P=a halogen, preferably Br, include using butyl vinyl ether and triethylamine in acetonitrile solvent at reflux temperature and at ambient/atmospheric pressure in the presence of catalyst such as palladium acetate and ligand such as tri-o-tolyl phosphine. For such reactions suitable reagent amount are (i) the ratio of base to compound (VI) is more than about 1.5:1, preferably more than about 2.0:1 and more preferably about 2.5:1 molecular equivalents and/or; (ii) the ratio of acylating agent to compound (VI) is about 2.5:1 to about 5:1, preferably about 2.5:1 to about 3.5:1 and especially about 3:1 molecular equivalents. Especially preferred herein for the provision of high yield of (XI) are such reactions wherein in addition to the aforementioned preferred ratios of acid (VI) to base and/or acylating agent, the ratio of acid (VI) to catalyst is about 1:0.04 molecular equivalents.

It is especially surprising that the above highly preferred conditions furnished higher yields of (IX) versus similar reactions where a higher catalyst level was utilised.

Following the initial reaction of compound (VI) with the base, acylating agent and catalyst in an appropriate solvent it is necessary that the reaction mixture is subjected to an aqueous acidic work-up in order to furnish the desired compound of formula (IX) rather than the intermediate enol-ether (VI') as detailed hereinbefore.

Reaction Scheme 3 illustrates the preparation of compounds of general formula (XI).

SCHEME 3

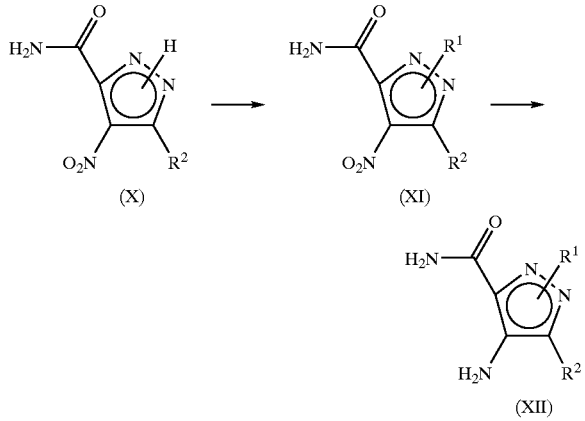

wherein $R^1$ and $R^2$ are as defined hereinbefore.

With reference to Scheme 3 compounds of formula (XII) can be formed from compounds of formula (XI) via a suitable reduction reaction such as with palladium on charcoal and hydrogen, under pressure where necessary. Compounds of formula (XI) can be formed from compounds of formula (X) via a suitable alkylation, arylation or acylation reaction.

Reaction Schemes 4 to 6 provide the corresponding intermediate compounds and transformations for the preparation of highly preferred compound (IA).

Scheme 4 illustrates a preferred process for the coupling of preferred compounds (IXA) and (XIIA) to provide compound of formula (IIIA) which are then cyclised to provide the compound of formula (IA) according to the process of the present invention.

SCHEME 4

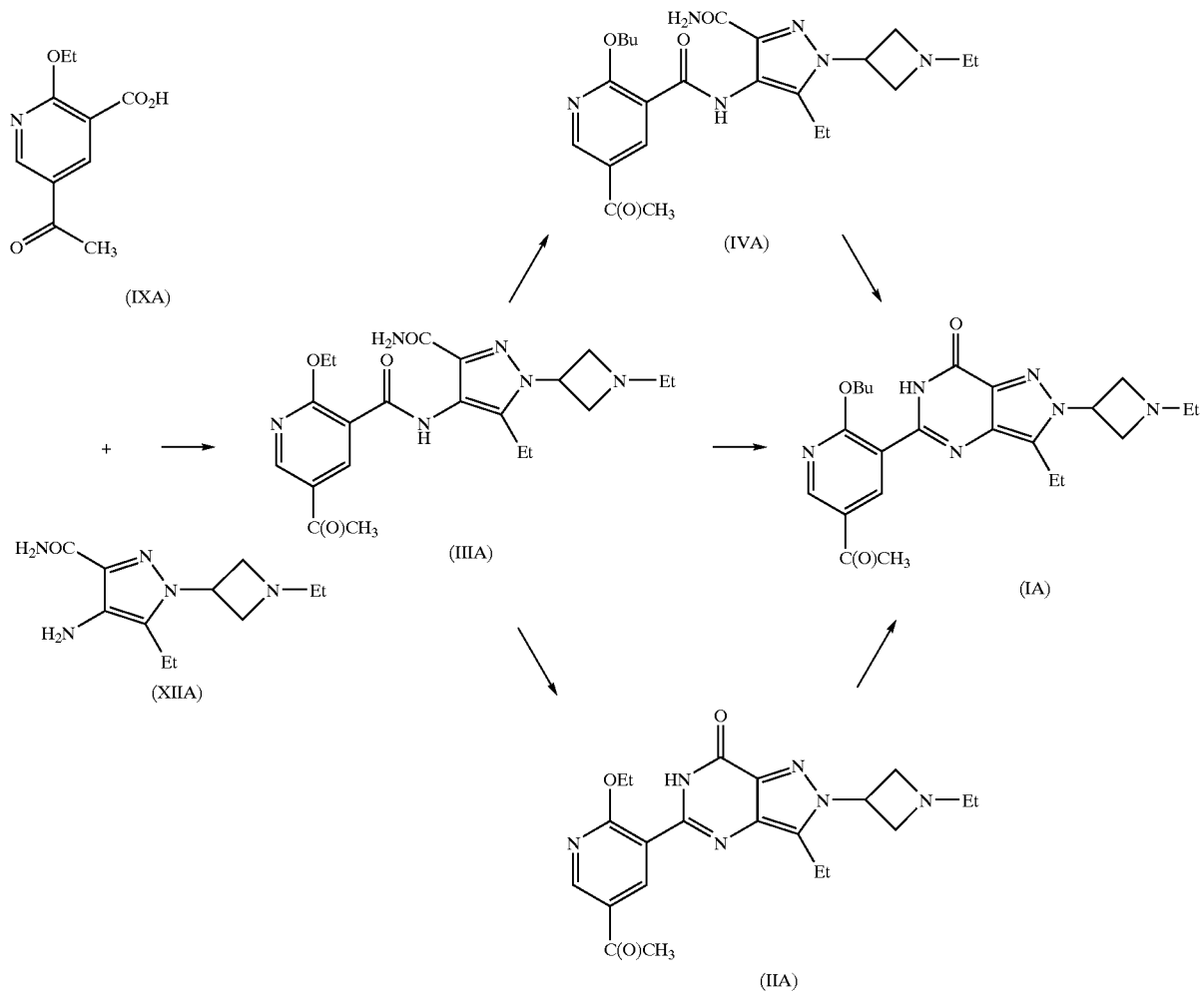

Reaction Scheme 5 illustrates a preferred process for the preparation of compounds of formula (IXA).

SCHEME 5

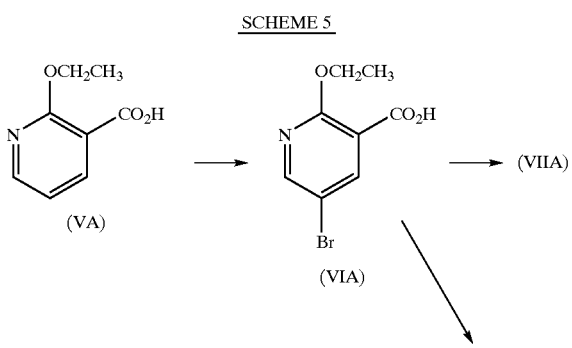

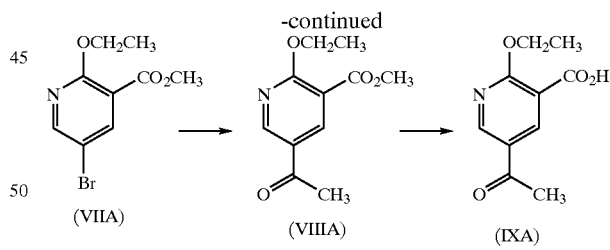

Scheme 5 illustrates a preferred embodiment for the formation of compound (IX) as generally described in Scheme 2, wherein X is an alkoxy (and so X in compound VA represents $OR^{3a}$), more preferably a $C_{1-6}$ primary or secondary alkoxy, such as ethoxy.

Compounds of the general formula (IXA) are prepared according to methods shown in Examples section hereinafter.

According to a highly preferred process herein compound (IXA) is prepared directly from compound (VIA) by reaction with acylating agent, base and catalyst wherein the ratio of compound (VIA):acylating agent:base:catalyst is about 1:3:2.5:0.04 molecular equivalents. In an especially preferred process the acylating agent is butyl vinyl ether, the base is triethylamine, the catalyst is Pd(OAc)₂, the solvent is acetonitrile and the ligand is tri-o-tolyl phosphine and the reaction is carried out under reflux conditions at atmospheric pressure. Such preferred process is illustrated at preparation 1(b) hereinafter.

Reaction Scheme 6 illustrates the preparation of compounds of general formula (XIIA) as generally detailed in Scheme 3.

Na(OAc)₃ BH to furnish the desired compound of formula (XIA) and as exemplified herein at preparation 8 hereinafter.

Compounds of formula (XIDP) can be formed from compounds of formula (XIP) via de-protection of the N-protecting benzhydryl group using suitable de-protection conditions such as exemplified at preparation 7 hereinafter.

Compounds of formula (XIP) can be formed from compounds of formula (XA) according to the processes at

SCHEME 6

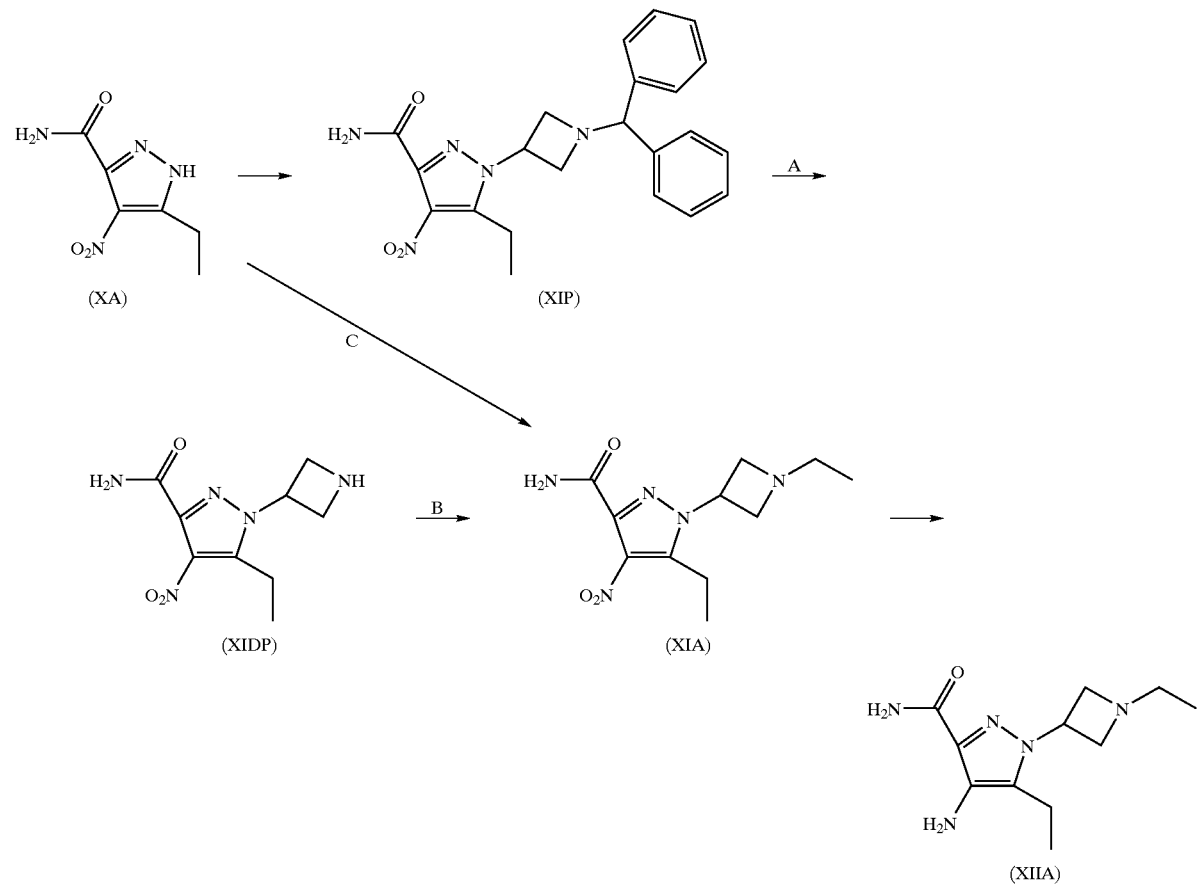

Compounds of formula (XIIA) can be formed from compounds of formula (XIA) via hydrogenation such as via treatment with palladium/charcoal and hydrogen and as exemplified herein at preparation 9 hereinafter.

Compounds of formula (XIA) can be formed from compounds of formula (XIDP) via a two stage process of: (i) amination (to prepare an intermediate imine of general formula (XIDP') as illustrated below:

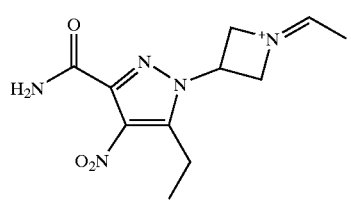

XIDP' such as via treatment with acetaldehyde or a synthetic equivalent followed by; (ii) reduction such as with preparations 6(a) and 6(b) hereinafter. The process of preparation 6(b) is particularly preferred herein as it provides higher yields.

According to a further aspect of the process hereinbefore described for the preparation of compounds of the general formula (XIA), such compounds can be prepared from compounds (XA) via a "one-step" process via reaction with the compound:

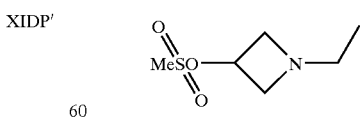

wherein such reaction takes place in a suitable non nucleophilic solvent, such as for example THF.

According to a particularly preferred process herein compounds of the general formula (XIA) can be prepared directly from compounds of the formula (XA). An advantage of such direct transformation is process efficiency.

Compound (IIIA) is formed by reaction of intermediate (IX) and 4-Amino-5-ethyl-1(2-ethyl-azetidinyl)-1H-pyrazole-3-carboxamide (compound XII) in the presence of a coupling agent, such as 1-(3-dimethylaminopropyl)-3-ethyl carbodiimide hydrochloride and where desirable also in the presence of a base and/or an accelerator. In one example of a coupling system, the carboxylic acid function of (VIA) is first of all activated using molar equivalent of a reagent such as N,N'-carbonyldimidazole (as coupling agent) in a suitable solvent, e.g. ethyl acetate, at from about room temperature to about 80° C., followed by reaction of the intermediate imidazolide with (XIIA) at from about 35 to about 80° C. In another example, intermediate (IXA) could be coupled to the pyrazole (XIIA) in the presence of 1-hydroxybenzotriazole, triethylamine and 1-(3-dimethylaminopropyl)-3-ethyl-carbodiimide hydrochloride.

It will be appreciated that salts of compounds (I) and (IA) of Schemes 1 and 4 can be formed in accordance with the invention by converting the relevant compound to a salt thereof (either in situ or as a separate step). For example base addition salts of the compounds of formulae (VI) and (XI) can be formed and can be utilised in accordance with the process of the present invention. Also the acid addition salts of the compounds of formulae (I) and (IA) can be formed in accordance with the invention.

By way of illustration, acid addition salts of compounds of formula (I) (more particularly (IA)) can be formed by reacting a compound of formula (I) with an equimolar or excess amount of acid. The salt may then be precipitated out of solution and isolated by filtration or the solvent can be stripped off by conventional means.

The pharmaceutically or veterinarily acceptable salts of the compounds of formulae (I) and (IA) which contain a basic centre are, for example, non-toxic acid addition salts formed with inorganic acids such as hydrochloric, hydrobromic, hydroiodic, sulphuric and phosphoric acid, with carboxylic acids or with organo-sulphonic acids. Examples include the HCl, HBr, HI, sulphate or bisulphate, nitrate, phosphate or hydrogen phosphate, acetate, benzoate, succinate, saccarate, fumarate, maleate, lactate, citrate, tartrate, gluconate, camsylate, methanesulphonate, ethanesulphonate, benzenesulphonate, p-toluenesulphonate and pamoate salts. Compounds (I) and (IA) can also provide pharmaceutically or veterinarily acceptable metal salts, in particular non-toxic alkali and alkaline earth metal salts, with bases. Examples include the sodium, potassium, aluminium, calcium, magnesium, zinc and diethanolamine salts. For a review on suitable pharmaceutical salts see Berge et al J. Pharm, Sci., 66, 1–19, 1977.

The pharmaceutically acceptable solvates of compounds (I) and (IA) include the hydrates thereof.

Suitable protecting groups for use in accordance with the invention can be found in "Protecting Groups" edited by P. J. Kocienski, Thieme, N.Y., 1994 —see particularly chapter 4, page 118–154 for carboxy protecting groups; and "Protective Groups in Organic Synthesis" 2$^{nd}$ edition, T. W. Greeene & P. G. M. Wutz, Wiley—Interscience (1991)—see particularly chapter 5 for carboxy protecting groups.

The process according to the present invention will now be described by way of example only with reference to the following examples.

Preparation 1—5-Acetyl-2-ethoxynicotinic acid

Preparation 1(a) Starting Material—5-Bromo-2-ethoxynicotinic acid (Preparation of VIA from VA)

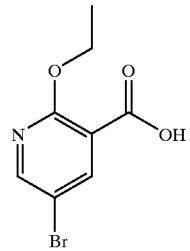

A solution of potassium t-butoxide (183.6 g, 1.60 mol) in absolute ethanol (1200 mL) as added slowly to a solution of 2-chloronicotinic acid (120 g, 0.76 mol) in ethanol (400 mL), and the reaction heated in a sealed vessel at 170° C. for 20 h. On cooling, the reaction mixture was concentrated under reduced pressure, the residue dissolved in water (800 mL) and acidified to pH 3 with aqueous hydrochloric acid. The aqueous solution was extracted with dichloromethane (4×800 mL), the organic phases combined, dried (Na$_2$SO$_4$) and concentrated under reduced pressure to afford the 2-ethoxy nicotinic acid (109.6 g, 41%) as a white solid [$^1$H NMR (300 MHz, CDCl$_3$): δ=1.53 (t, 3H), 4.69 (q, 2H), 7.13 (m, 1H), 8.37 (d, 1H), 8.48 (d, 1H)]. 2-Ethoxynicotinic acid (83.6 g, 0.5 mol) was added portionwise to a mixture of trifluoroacetic acid/trifluoroacetic anhydride (TFA/TFAA) (350 mL of each) at room temperature with constant stirring. N-Bromo-succinamide (NBS) (89.0 g, 0.5 mol) was then added portionwise over 20 minutes before the reaction mixture was heated to reflux for 5 hours. The reaction was cooled to room temperature and allowed to stir overnight. The reaction was then poured into a 1:1 mixture of cooled brine/water (2 L). The resultant white solid was filtered, washed with water and dissolved in EtOAc (300 mL). The solution was dried over MgSO$_4$ and filtered. The filtrate was treated with hexane (1.2 L) and the resultant pale yellow precipitate was filtered and washed with 40–60 petroleum ether. The title compound was dried at 50° C. under vacuum: m.p.=122–124° C; 1H NMR (300 MHz, CDCl$_3$): δ=1.53 (t, 3H), 2.64 (s, 3H), 4.67 (q, 2H), 8.42 (d, 1H), 8.57 (d, 1H).

Preparation 1(b)—5-Acetyl-2-ethoxynicotinic acid (Preparation of IXA from VIA)

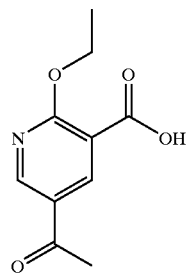

Triethylamine (354 mL, 2.54 M), was added to a slurry of 5-bromo-2-ethoxynicotinic acid (250 g, 1.02 M) in acetonitrile (1 L). To this reaction mixture was added palladium (II) acetate (4.56 g, 20.3 mmol), butyl vinyl ether (305 g, 3.05 M) and tri-o-tolyl phosphine (12.4 g, 40.6 mmol), each addition being washed in with acetonitrile. Further acetonitrile (1 L) was then added and the reaction mixture heated to reflux under nitrogen for 22 hours. The reaction mixture was left at room temperature for 16 hours, and then the precipitate removed by filtration. The filtrate was concentrated in vacuo to give a brown gum, which was then stirred for 1 hour in water (1 L) and concentrated HCl (1 L). The reaction mixture was diluted with water (6.25 L), and extracted with dichloromethane (6×500 mL). The combined organic layers were extracted with 5% sodium bicarbonate solution (1.2 L, 2×400 mL). The basic aqueous extracts were washed with dichloromethane (250 mL), and then acidified to pH 3. After stirring for 30 minutes the precipitated product was removed by filtration, washed with water (250 mL) and dried at 50° C. in vacuo to yield the target compound as a white solid (134 g, 64.1 mmol, 63%): 1H NMR (400 MHz, CDCl$_3$): δ=1.56 (t, 3H, J=7.1 Hz), 2.64 (s, 3H), 4.78 (q, 2H, J=6.7 Hz), 8.96 (1H, J=2.6 Hz), 8.98 (d, 1H, J=2.6 Hz); LRMS (m/z) (ES$^-$) 208 (MH$^-$).

Preparation 2

5-Acetyl-N-[3-(aminocarbonyl)-5-ethyl-1-(1-ethyl-3-azetidinyl)-1H-pyrazol-4-yl]-2-ethoxynicotinamide Preparation 2(a)

1-(1-Benzhydryl-3-azetidinyl)-5-ethyl-4-nitro-1H-pyrazole-3-carboxamide

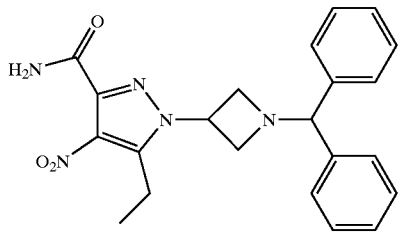

The title compound was prepared by either of the following methods;

a) 5-Ethyl-4-nitro-1H-pyrazole-3-carboxamide (WO 98/49166) (25.0 g, 136 mmol), sodium carbonate (57.6 g, 543 mmol), sodium iodide (40.7 g, 272 mmol) and 1-benzhydryl-3-azetidinyl methanesulfonate (86.2 g, 272 mmol) were suspended in tetrahydrofuran (338 mL) and water (38 mL) and heated under reflux for 5 days. The reaction mixture was then concentrated in vacuo and taken up in ethyl acetate (500 mL) and water (300 mL). The resulting precipitate was filtered, washed with ethyl acetate and water to yield the title compound as a white solid (17 g, 41.9 mmol, 31%): mp 257–260° C.; 1H NMR (400 MHz, DMSO-d$_6$): δ=1.09 (t, 3H, J=7.6 Hz), 2.95 (q, 2H, J=7.3 Hz), 3.43 (t, 2H, J=7.6 Hz), 3.61 (t 2H, J=7.6 Hz), 4.59 (s, 1H), 5.23 (quintet, 1H, J=7.3 Hz), 7.15–7.20 (m, 2H), 7.24–7.31 (m, 4H), 7.43–7.48 (m, 4H), 7.70 (br s, 1H), 7.95 (br s, 1H); LRMS (m/z) (TSP$^+$) 406.2 (MH$^+$).

b) 5-Ethyl-4-nitro-1H-pyrazole-3-carboxamide[1] (800.0 g, 4.34 mol), sodium carbonate (1845 g, 17.4 mol), sodium iodide (965 g, 6.44 mol) and 1-benzhydryl-3-azetidinyl methanesulfonate (1837 g, 5.8 mol) were suspended in tetrahydrofuran (10.8 L) and water (1.2 L) and heated under reflux for 5 days with constant stirring. The reaction mixture was then distilled at atmospheric pressure so that 7.5 L of solvent was distilled. The reaction was cooled to 40° C. and water (8 L) was added to the reaction mixture. The reaction mixture was again heated while solvent was distilled at atmospheric pressure. In this distillation the internal temperature rose to 9° C. and 900 mL of solvent was collected. The reaction was cooled to 80° C. and MIBK (2.4 L) was added the reaction mixture was then heated to reflux for 1 h and allowed to cool to room temperature overnight. The resulting precipitate was cooled to 12° C. and granulated for 2 hours before filtering. The filter cake was washed with water (2 L) and MIBK (2 L). The solid product was oven dried at 50° C. under vacuum. The resultant yellow solid was reslurried in water (9 L) at room temperature for 3 hours before being filtered under vacuum. The filter cake was washed with MIBK (1 L) with gentle agitation using a spatula. The pale cream solid was oven dried at 50° C. under vacuum to afford the title compound (758 g, 43%): Data as reported above.

Preparation 2(b)

1-(3-Azetidinyl)-5-ethyl-4-nitro-1H-pyrazole-3-carboxamide

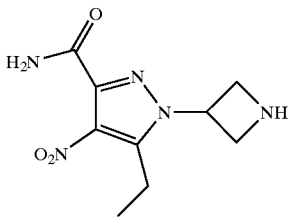

To a suspension of the title compound of Preparation 2(a) (35.3 g, 87.1 mmol) in dichloromethane (700 mL) at 0° C. under nitrogen was added 1-chloroethyl chloroformate (10.4 mL, 95.8 mmol) dropwise. The reaction mixture was stirred at 0° C. for 30 minutes, and at room temperature for 18 hours. The reaction mixture was then concentrated in vacuo, and the oily residue dissolved in methanol (700 mL) and refluxed for 1 hour. The solvent was then removed in vacuo, and the crude product triturated from ethyl acetate (200 mL) and acetone (200 mL) to yield the dihydrochloride salt of the title compound as a beige solid (21.3 g, 77.3 mmol, 89%): mp 164–167° C; 1H NMR (400 MHz, DMSO-d$_6$): δ=1.09 (t, 3H, J=7.6 Hz), 2.92 (q, 2H, J=7.3 Hz), 4.26–4.40 (m, 4H), 4.44–4.51 (m, 1H), 7.75 (br s, 1H), 8.01 (br s, 1H), 9.39 (br s, 2H); LRMS (m/z) (TSP$^+$) 240.3 (MH$^+$).

Preparation 2(c)

5-Ethyl-1-(1-ethyl-3-azetidinyl)-4-nitro-1H-pyrazole-3-carboxamide

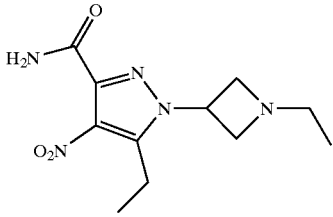

To a stirring solution of the title compound of Preparation 2(b) (31.1 g, 113 mmol) and triethylamine (14.1 mL, 102 mmol) in dichloromethane (400 mL) and methanol (400 mL) at 0° C., was added sodium triacetoxyborohydride (60 g, 282 mmol) in one portion. Acetaldehyde (19 mL, 339 mmol) was then added dropwise over 2 minutes. The reaction mixture was then allowed to warm up to room temperature over 30 minutes. The solvent was then removed in vacuo, and the residue partitioned between dichloromethane (500 mL) and water (300 mL). The organic layer was separated, and the aqueous layer basified with solid sodium bicarbonate and extracted with dichloromethane (500 mL) and dichloromethane:methanol (95:5, 500 mL; 90:10, 500 mL). The combined organic layers were dried (MgSO$_4$), and concentrated in vacuo. The residue was triturated from hot ethyl acetate, and a white solid separated by filtration. The filtrate was concentrated in vacuo, and purified by flash column chromatography (eluting with CH$_2$Cl$_2$:MeOH:0.88NH$_3$ 95:5:0.5) to give a white solid which was combined with the previous batch to yield the title compound (23.3 g, 86.8 mmol, 77%): mp 177–179° C.; 1H NMR (400 MHz, CDCl$_3$): δ=1.01 (t, 3H, J=7.3 Hz), 1.25 (t, 3H, J=7.6 Hz), 2.62 (q, 2H, J=7.3 Hz), 2.95 (q, 2H, J=7.8 Hz), 3.55 (dt, 2H, J=2.0, 6.4 Hz), 3.83 (dt, 2H, J=2.0, 6.8 Hz), 4.96 (quintet, 1H, J=7.3 Hz), 6.13 (br s, 1H), 6.92 (br s, 1H); LRMS (m/z) (TSP$^+$) 268.3 (MH$^+$).

Preparation 2(d)

4-Amino-5-ethyl-1-(1-ethyl-3-azetidinyl)-1H-pyrazole-3-carboxamide

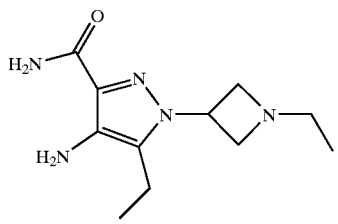

A mixture of the title compound from Preparation 2(c) (22.0 g, 82.3 mmol) and 10% palladium on charcoal (2.0 g) in ethanol (500 mL) was hydrogenated at 60 p.s.i. and room temperature for 4 hours. The reaction mixture was then filtered through Arbocel ® under nitrogen, and the filtrate was concentrated in vacuo to yield the title compound as a cream solid (19.6 g, 82.6 mmol, 100%): mp 155–157° C; 1H NMR (400 MHz, CDCl$_3$): δ=1.01 (t, 3H, J=7.2 Hz), 1.13 (t, 3H, J=7.6 Hz), 2.54 (q, 2H, J=7.8 Hz), 2.59 (q, 2H, J=7.3 Hz), 3.46 (t, 2H, J=7.8 Hz), 3.77 (t, 2H, J=7.6 Hz), 3.93 (br s, 2H), 4.83 (quintet, 1H, J=7.3 Hz), 5.25 (br s, 1H), 6.64 (br s, 1H); LRMS (m/z) (TSP$^+$) 238.2 (MH$^+$).

Preparation 2(e)

5-Acetyl-N-[3-(aminocarbonyl)-5-ethyl-1-(1-ethyl-3-azetidinyl)-1H-pyrazol-4-yl]-2-ethoxynicotinamide

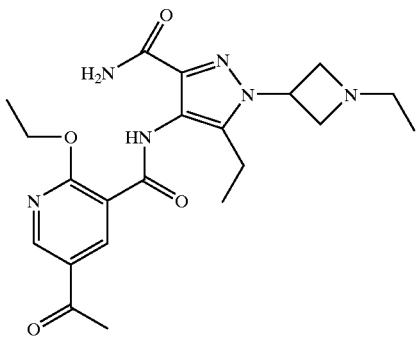

1,1-Carbonyldiimidazole (13.9 g, 85.8 mmol) was added to a suspension of the title compound from Preparation 1(b) (17.1 g, 81.8 mmol) in ethyl acetate (140 mL) under nitrogen, and the reaction mixture was stirred at 45° C. for 45 minutes and heated under reflux for 90 minutes. The reaction mixture was then cooled to room temperature and a slurry of the title compound from Preparation 9 (19.4 g, 81.8 mmol) in ethyl acetate (70 mL) was added. The reaction mixture was then heated under reflux for 16 hours, after which a precipitate had formed. The suspension was cooled to room temperature and the solid removed by filtration. The solid was washed with water:ethanol 90:10 and then dried in vacuo to yield the title compound as a white solid (24.0 g, 56.0 mmol, 69%): mp 230–233° C.; 1H NMR (400 MHz, CDCl$_3$): δ=1.03 (t, 3H, J=7.3 Hz), 1.20 (t, 3H, J=7.8 Hz), 1.57 (t, 3H, J=7.3 Hz), 2.60 (s, 3H), 2.62 (q, 2H, J=6.8 Hz), 2.86 (q, 2H, J=7.3 Hz), 3.53 (t, 2H, J=7.8 Hz), 3.83 (t, 2H, J=7.3 Hz), 4.77 (q, 2H, J=6.8 Hz), 4.99 (quintet, 1H, J=7.3 Hz), 5.30 (br s, 1H), 6.74 (br s, 1H), 8.89 (d, 1H, J=2.4 Hz), 9.02 (d, 1H, J=2.4 Hz), 10.48 (br s, 1H); LRMS (m/z) (TSP$^+$) 429.2 (MH$^+$).

Preparation 3

2-Propoxynicotinic acid

Sodium metal (9.2 g, 0.4 mol), washed free of oil (with hexane), was added in small pieces, over 2 h, to anhydrous n-propanol (350 mL) whilst maintaining a temperature between 50° C. and 100° C. To the resultant clear, yellow solution was added a slurry of 2-chloronicotinic acid (31.5 g, 0.2 mol) in anhydrous propanol (100 mL), and the suspension heated to reflux for 6 h. The bulk of the solvent was distilled off, and replaced, after cooling, with diethyl ether (200 mL) to afford a thick white solid which was removed by filtration and washed with diethyl ether (500 mL). The solid was taken up in water (300 mL), washed with dichloromethane (200 mL), and the aqueous phase acidified with concentrated hydrochloric acid to pH 4.5 and extracted with dichloromethane (3×200 mL). The combined extracts were washed with brine, dried over MgSO$_4$, and concentrated to an oil (40 g). The oil was taken up in pentane (150 mL) and stood in ice for 30 mins to deliver a white crystalline solid which was collected by filtration, washed with fresh pentane (3×200 mL) and dried under vacuum to afford 2-propoxynicotinic acid (26.5 g, 146 mmol).

$^1$H NMR (300 MHz, d6DMSO+1 drop $d_1$-trifluoroacetic acid) δ=0.95 (t, 3H), 1.65–1.8 (m, 2H), 4.25 (t, 2H), 7.0 (m, 1H), 8.1 (d, 1H), 8.25 (d, 1H).

Preparation 4

2-Propoxy-5-iodonicotinic acid

The title compound from Preparation 3 (9.30 g, 51.3 mmol) was dissolved slowly in trifluoroacetic acid (75 mL) and trifluoroacetic anhydride (19 mL). N-iodosuccinimide (18.6 g, 82.7 mmol) was then added portionwise, and the red/brown solution heated at reflux for 6 h followed by 16 h at room temperature. The reaction mixture was then concentrated in vacuo and water (150 mL) added. The aqueous mixture was extracted with dichloromethane (3×150 mL). The combined organic layers were extracted with aqueous sodium hydroxide solution (1 N, 200 mL), and then the aqueous acidified with concentrated hydrochloric acid. The acidic aqueous layer was then extracted with dichloromethane (4×150 mL), the combined organic layers washed with brine (150 mL), dried (MgSO$_4$) and concentrated in vacuo. Trituration from pentane yielded the target compound as an off-white solid (11.3 g, 36.8 mmol):

1H NMR (300 MHz, CDCl$_3$): δ 1.05 (t, 3H, J=7.6 Hz), 1.86–1.95 (m, 2H), 4.60 (t, 2H, J=7.0 Hz), 8.55 (d, 1H, J=2.4 Hz), 8.70 (d, 1H, J=2.7 Hz);

LRMS (m/z) (ES$^-$): 306 (MH$^-$).

Preparation 5

N-[3-(Aminocarbonyl)-5-ethyl-1H-pyrazol-4-yl]-5-iodo-2-propoxy-nicotinamide

The title compound from Preparation 4 (16 g, 52.1 mmol) was suspended in dichloromethane (160 mL) and cooled to 0° C. Oxalyl chloride (13 mL, 1.49 mol) was then added followed by a drop of N,N-dimethylformamide, and the reaction mixture allowed to warm up to room temperature. After 2 h the reaction mixture was concentrated in vacuo, and azeotroped with dichloromethane (×2). The residue was then dissolved in dichloromethane (160 mL) and 4-amino-3-ethyl-1H-pyrazole-5-carboxamide (prepared as described in WO 98/49166) (8.5 g, 55.1 mmol) and triethylamine (20.8 mL, 1.49 mol) were added at 0° C. The reaction mixture was allowed to warm up to room temperature and stirred for 16 h under nitrogen. The reaction mixture was then diluted with water (150 mL) and dichloromethane (150 mL), and the precipitate removed by filtration. The precipitate was washed well with dichloromethane and water to yield the title compound. The combined organic filtrates were then washed with aqueous hydrochloric acid (2M, 75 mL), saturated aqueous sodium bicarbonate solution (75 mL), brine (100 mL), dried (MgSO$_4$) and concentrated in vacuo. The resulting crude product was triturated from ethyl acetate to give a white solid. This solid was combined with the previous residue to yield the title compound as a white solid (17.1 g, 38.6 mmol).

$^1$H NMR (300 MHz, $d_4$-methanol): δ 1.0 (t, 3H), 1.25 (t, 3H), 1.85–2.0 (m, 2H), 2.8 (q, 2H), 4.5 (t, 2H), 8.5 (s, 1H), 8.6 (s, 1H).

LRMS (TSP) 444 (MH$^+$).

Preparation 6

2-Ethoxynicotinic acid

A solution of potassium t-butoxide (44.9 g, 0.40 mol) in absolute ethanol (300 mL) was added slowly to a solution of 2-chloronicotinic acid (30 g, 0.19 mol) in ethanol (100 mL), and the reaction heated in a sealed vessel at 170° C. for 20 h. On cooling, the reaction mixture was concentrated under reduced pressure, the residue dissolved in water (200 mL) and acidified to pH 3 with aqueous hydrochloric acid. The aqueous solution was extracted with dichloromethane (4×200 mL), the organic phases combined, dried (Na$_2$SO$_4$) and concentrated under reduced pressure to afford the title compound (27.4 g, 16.4 mmol) as a white solid.

$^1$H NMR (300 MHz, CDCl$_3$): δ 1.53 (t, 3H), 4.69 (q, 2H), 7.13 (m, 1H), 8.37 (d, 1H), 8.48 (d, 1H).

Preparation 7

2-Ethoxynicotinic acid ethyl ester

A suspension of the title compound of Preparation 6 (16.4 g, 98 mmol), and cesium carbonate (32 g, 98 mmol) in N,N-dimethylformamide (240 mL) was stirred at room temperature for 2 h. Ethyl iodide (7.85 mL, 98 mmol) was added and the reaction stirred for a further 24 h. The reaction mixture was concentrated under reduced pressure and the residue partitioned between aqueous sodium carbonate solution (100 mL) and ethyl acetate (100 mL). The phases were separated and the aqueous phase extracted with ethyl acetate (2×100 mL). The combined organic solutions were washed with brine, dried (Na$_2$SO$_4$) and evaporated under reduced pressure to afford the title compound (18.0 g, 92.2 mmol) as a pale yellow oil.

$^1$H NMR (300 MHz, CDCl$_3$): δ 1.41 (m, 6H), 4.36 (q, 2H), 4.48 (q, 2H), 6.90 (m, 1H), 8.12 (d, 1H), 8.28 (d, 1H).

Preparation 8

Pyridine-2-ethoxy-5-nitro-3-carboxylic acid ethyl ester

Ammonium nitrate (5.36 g, 66 mmol) was added portionwise to an ice-cooled solution of the title compound of Preparation 7 (4.66 g, 22.3 mmol) in trifluoroacetic anhydride (50 mL) and the reaction stirred for 18 h at room temperature. The reaction mixture was carefully poured into ice water (200 mL) and the resulting suspension stirred for an hour. The precipitate was filtered off, washed with water and dried under suction to afford the title compound (3.29 g, 13.7 mmol).

$^1$H NMR (300 MHz, CDCl$_3$): δ 1.41 (t, 3H), 1.48 (t, 3H), 4.41 (q, 2H), 4.62 (q, 2H), 8.89 (s, 1H), 9.16 (s, 1H).

Preparation 9

Pyridine-2-ethoxy-5-nitro-3-carboxylic acid

Aqueous sodium hydroxide solution (4 mL, 5N, 20 mmol) was added dropwise to a solution of the title compound of Preparation 8 (5.1 g, 20 mmol) in ethanol (100 mL) and the reaction stirred at room temperature for 18 h. The reaction mixture was concentrated in vacuo, the residue suspended in water (50 mL) and acidified to pH 3 with hydrochloric acid. This aqueous solution was extracted with ethyl acetate (3×100 mL), the combined organic layers washed with brine (100 mL), dried (Na$_2$SO$_4$) and evaporated under reduced pressure to give a beige solid. The crude product was recrystallised from ethyl acetate/hexane to afford the title compound (3.32 g, 15.6 mmol) as beige crystals.

$^1$H NMR (300 MHz, CDCl$_3$): δ 1.55 (t, 3H), 4.78 (q, 2H), 9.17 (s, 1H), 9.23 (s, 1H).

Preparation 10

N-[5-(Aminocarbonyl)-1-methyl-3-propyl-1H-pryrazol-4-yl]-2-ethoxy-5-nitronicotinamide The product of Preparation 9 and 4-amino-1-methyl-3-propyl-1H-pyrazole-5-carboxamide (prepared as described in EP 526 004) were combined using the method of Preparation 5.

m.p. 251–3° C.

1H NMR (300 MHz, $d_6$-DMSO): δ 0.9 (t, 3H), 1.38 (t, 3H), 1.5–1.7 (m, 2H), 2.5–2.55 (m, partially obscured by DMSO peak, 2H), 3.9 (s, 3H), 4.5–4.65 (m, 2H), 7.3 (br s, 1H), 7.7 (brs, 1H), 8.7 (s, 1H), 9.2 (s, 1H), 9.7 (s, 1H).

LRMS (ES negative ion) 375 (M–H)⁻.

Analysis: Found C, 50.99; H, 5.36; N, 22.33. Calcd for $C_{16}H_{20}N_6O_5$: C, 51.06; H, 5.36; N, 22.33%.

Preparation 11a

3-Ethyl-1-[2-(4-morpholinyl)ethyl]-4-nitro-1H-pyrazole-5-carboxamide and

Preparation 11b

5-Ethyl-1-[2-(4-morpholinyl)ethyl]-4-nitro-1H-pyrazole-3-carboxamide

A mixture of 3-ethyl-4-nitro-1H-pyrazole-5-carboxamide (prepared as in WO 98/49166) (20.0 g, 0.11 mol), potassium carbonate (29.9 g, 0.22 mmol) and cesium carbonate (7.08 g, 21.7 mmol) were stirred together at room temperature. After 15 minutes 4(2-chloroethyl)morpholine.HCl (22.2 g, 0.12 mol) was added and the reaction mixture was heated at 55° C. for 16 h. The reaction mixture was concentrated in vacuo, and then partitioned between water (500 mL) and ethyl acetate (350 mL). Solid sodium carbonate was added until the pH reached 10, and then the organic layer was separated. The aqueous layer was extracted with further ethyl acetate (150 mL). The combined organic layers were concentrated in vacuo, combined with 1.6 g of a previous identical batch and purified by flash column chromatography (eluting with methanol:ethyl acetate:NH₃ 0:100:0 to 20:80:1). Two products were separated. The first product was triturated from diethyl ether to yield 3-ethyl-1-[2-(4-morpholinyl)ethyl]-4-nitro-1H-pyrazole-5-carboxamide as cream coloured crystals (16.2 g, 54.5 mmol).

m.p. 133° C.

¹H NMR (400 MHz, CDCl₃): δ 1.25 (t, 3H), 2.43 (t, 4H), 2.79 (t, 2H), 2.90 (q, 2H), 3.60 (t, 4H), 4.45 (t, 2H), 6.40 (br s, 1H), 7.63 (br s, 1H).

LRMS (TSP) 297.9 (MH⁺).

Analysis: Found C, 48.47; H, 6.47; N, 23.49. Calcd for $C_{12}H_{19}N_5O_4$: C, 48.48; H, 6.44; N, 23.56%.

The second product was triturated from ethyl acetate to yield 5-ethyl-1-[2-(4 morpholinyl)ethyl]-4-nitro-1H-pyrazole-3-carboxide as white crystals (7.83 g, 26.3 mmol).

m.p. 144.9–147.1° C.

¹H NMR (400 MHz, CDCl₃): δ 1.30 (t, 3H), 2.43 (t, 4H), 2.82 (t, 2H), 3.00 (q, 2H), 3.62 (t, 4H), 4.20 (t, 2H), 6.00 (br s, 1H), 7.22 (br s, 1H).

LRMS (TSP) 297.7 (MH⁺).

Analysis: Found C, 48.2; H, 6.43; N, 23.30. Calcd for $C_{12}H_{19}N_5O_4$: C, 48.48; H, 6.44; N, 23.56%.

The regiochemistry was determined by nOe studies.

Preparation 12

4-Amino-3-ethyl-1-[2-(4-morpholinyl)ethyl]-1H-pyrazole-5-carboxamide

The title compound of Preparation 11a (16 g, 54 mmol) was dissolved in ethanol (320 mL) and treated with 10% Pd on C (1.5 9) before stirring at room temperature under 60 psi of hydrogen for 6 h. The catalyst was removed by filtration through Arbocel®, the filtrate concentrated in vacuo to an oil which afforded the title compound as a pink solid after trituration with diisopropyl ether (13.18 g, 49.3 mmol).

m.p. 115–7° C.

1H NMR (300 MHz, CDCl₃): δ=1.2 (t, 3H), 2.4–2.5 (m, 4H), 2.55 (q, 2H), 3.4 (s, 2H), 3.6–3.65 (m, 4H), 4.45 (t, 2H).

LRMS (TSP) 268 (MH⁺).

Analysis: Found C, 53.89; H, 8.04; N, 25.86. Calcd for $C_{12}H_{21}N_5O_2$: C, 53.92; H, 7.92; N, 26.20%.

Preparation 13

N-{5-(Aminocarbonyl)-3-ethyl-1-[2-(4-morpholinyl)ethyl]-1H-pyrazol-4-yl}-5-iodo-2-propoxynicotinamide The title compound was prepared by the method of Preparation 5 using the title compounds of Preparations 4 and 12.

m.p. 180–180.5° C.

1H NMR (300 MHz, CDCl₃): δ=1.05 (t, 3H), 1.25 (t, 3H), 1.85–1.95 (m, 2H), 2.4–2.55 (m, 4H), 2.6 (q, 2H), 2.8 (t, 2H), 3.55–3.7 (m, 4H), 4.5 (t, 2H), 4.55 (t, 2H), 5.6 (br s, 1H), 8.25 (br s 1H), 8.5 (s, 1H), 8.75 (s, 1H), 9.5 (s, 1H).

LRMS (TSP) 558 (MH⁺).

Analysis: Found C, 45.05; H, 5.23; N, 14.59. Calcd for $C_{21}H_{29}N_6O_4I.0.2H_2O$: C, 45.04; H, 5.29; N, 15.01%.

Preparation 14

2-Ethoxy-5-iodonicotinic acid

The title compound was prepared from 2-ethoxynicotinic acid using the method of Preparation 4.

¹H NMR (400 MHz, $d_6$-DMSO): δ=1.3 (t, 3H), 4.35 (q, 2H), 8.3 (d, 1H), 8.5 (d, 1H), 13.2 (br s, 1H).

Preparation 15

N-[5-(Aminocarbonyl)-3-ethyl-1H-pyrazol-4-yl]-2-ethoxy-5-iodonicotinamide

The title compound of Preparation 14 (8 g, 27.3 mmol) in dichloromethane (200 mL) was treated with 1-hydroxybenzotriazole hydrate (4.43 g, 32.8 mmol), N,N-diisopropylethylamine (14.3 mL, 77.8 mmol), 1-(3-dimethylaminopropyl)-3-ethylcarbodiimide hydrochloride (6.27 g, 31.7 mmol) and 4-amino-3-ethyl-1H-pyrazole-5-carboxamide (prepared as described in WO 98/49166; 3.78 g, 24 mmol), and the resultant mixture stirred at room temperature for 14 h. After washing with water (100 mL), a portion of the title compound was isolated by filtration of the precipitate as a pale brown solid (6.55 g, 15.3 mmol). The organic phase was dried over MgSO₄, concentrated, and the residue treated with diethyl ether to give further title compound as a pale brown solid (1.65 g, 3.84 mmol).

¹H NMR (300 MHz, CDCl₃): δ=1.25 (t, 3H), 1.55 (t, 3H), 2.9 (2H, q), 2.65 (2H, q), 5.4 (brs, 1H), 6.75 (brs, 1H), 8.4 (d, 1H), 8.8 (d, 1H), 10.65 (brs, 1H).

LRMS (ES⁻ positive ion) 430 (MH⁺).

Preparation 16

N-[3-(Aminocarbonyl)-1-(4-cyanobenzyl)-5-ethyl-1H-pyrazol-4-yl]-2-ethoxy-5-iodonicotinamide The title compound from Preparation 15 (1.00 g, 2.33 mmol) was dissolved in tetrahydrofuran (25 mL) and cooled to 0° C. Sodium hydride (112 mg, 60% in mineral oil, 2.80 mmol) was then added, followed by 4-cyanobenzylbromide (548 mg, 2.8 mmol) after 30 minutes. The reaction mixture was heated at 60° C. for 16 h. The solvent was then removed in vacuo, and the residue partitioned between water (50 mL) and dichloromethane (50 mL). The organic phase was separated, dried (MgSO$_4$), and concentrated in vacuo. The crude product was purified by flash column chromatography (eluting with dichloromethane:methanol 100:1 to 95:5) to give the title compound (1.06 g, contaminated with low level of impurity). Taken on to next stage crude.

1H NMR (300 MHz, CDCl$_3$): δ=1.2 (t, 3H), 1.55 (t, 3H), 2.8 (q, 2H), 3.0 (s, 3H), 3.1 (s, 3H), 4.65 (q, 2H), 4.95 (s, 2H), 5.2 (br s, 1H), 6.6 (br s, 1H), 8.40 (d, 1H), 8.80 (d, 1H), 10.45 (br s, 1H).

LRMS (TSP) 514 (MH$^+$), 537 (MNa$^+$).

Preparation 17

N-[3-(Aminocarbonyl)-5-ethyl-1-(2-pyridinylmethyl)-1H-pyrazol-4-yl]-5-iodo-2-propoxynicotinamide The title compound was prepared using the method of Preparation 5 and the title compounds of Preparations 4 and 4-amino-5-ethyl-1-(2-pyridinylmethyl)-1H-pyrazole-3-carboxamide (WO 9849166). 1H NMR (400 MHz, CDCl$_3$): δ=1.00 (m, 6H), 1.90 (m, 2H), 2.80 (q, 2H), 4.50 (t, 2H), 5.20 (s, 1H), 5.40 (s, 2H), 6.60 (s, 1H), 6.90 (d, 1H), 7.20 (m, 1H), 7.60 (app. t, 1H), 8.40 (d, 1H), 8.60 (m, 1H), 8.75 (s, 1H), 10.40 (s, 1H).

LRMS (ES—positive ion) 535 (MH$^+$), (ES—negative ion) 533 (M–H).

Anal. Found C, 47.53; H, 4.41; N, 15.69. Calcd for C$_{21}$H$_{23}$O$_3$N$_6$I: C, 47.20; H, 4.34; N, 15.73.

Preparation 18 tert-Butyl 3-iodo-1-azetidinecarboxylate

A mixture of tert-butyl 3-[(methylsulfonyl)oxy]-1-azetidinecarboxylate (prepared as described in Synlett 1998, 379; 5.0 g, 19.9 mmol), and potassium iodide (16.5 g, 99.4 mmol) in N,N-dimethylformamide (25 mL), was heated at 100° C. for 42 h. The cooled to mixture was partitioned between water and ethyl acetate, and the layers separated. The organic phase was dried over MgSO$_4$, concentrated under reduced pressure and the residue azeotroped with xylene. The crude product was purified by flash column chromatography (dichloromethane as eluant) to give the title compound (3.26 g, 11.5 mmol).

$^1$H NMR (300 MHz, CDCl$_3$) =1.43 (s, 9H), 4.28 (m, 2H), 4.46 (m, 1H), 4.62 (m, 2H).

LRMS (TSP) 284 (MH)$^+$.

Preparation 19 tert-Butyl 3-3-(aminocarbonyl)-5-ethyl-4-{[(5-iodo-2-propoxy-3-pyridinyl)carbonyl]amino}-1H-pyrazol-1-yl)-1-azetidinecarboxylate The title compounds from Preparation 5 (5.00 g, 11.3 mmol) and Preparation 18 (3.84 g, 13.5 mmol) were stirred together in dry N,N-dimethylformamide (40 mL) at room temperature under nitrogen, and then cesium carbonate (4.41 g, 13.5 mmol) was added. The reaction mixture was stirred at room temperature for 2 h and then heated at 60° C. for 16 h. Further aliquots of the title compound from Preparation 18 (959 mg, 3.39 mmol) and cesium carbonate (1.10 g, 3.39 mmol) were then added and stirring continued for 24 h at 60° C. and 36 h at room temperature. The reaction mixture was then filtered to yield the title compound as a white solid (3.47 g). The filtrate was diluted with dichloromethane (100 mL), and washed with citric acid (10% aq., 2×30 mL), water (30 mL), then dried (MgSO$_4$) and concentrated in vacuo to yield an oil. The crude oil was purified by flash column chromatography (eluting with 99:1 to 97:3 dichloromethane:methanol) and trituration from hot ethyl acetate to yield the title compound as a white solid (900 mg). The two batches of title compound were combined (4.37 g, 7.30 mmol).

1H NMR (400 MHz, DMSO): δ=0.95 (t, 3H), 1.05 (t, 3H), 1.40 (s, 9H), 1.78–1.88 (m, 2H), 2.68 (q, 2H), 4.22–4.35 (m, 4H), 4.40 (t, 2H), 5.33 (t, 1H), 7.35 (bs, 1H), 7.52 (bs, 1H), 8.40 (s, 1H), 8.55 (s, 1H), 10.10 (s, 1H).

LRMS (TSP—positive ion) 373.2 (MH$^+$—BOC and I)

Anal. Found C, 45.11; H, 5.07; N, 13.56 Calcd for C$_{23}$H$_{31}$O$_5$N$_6$I.0.2 dichloromethane: C, 45.28; H, 5.14; N, 13.66.

Preparation 20 tert-Butyl 4-(3-(aminocarbonyl)-5-ethyl-4-{[(5-iodo-2-propoxy-3-pyridinyl)carbonyl]amino}-1H-pyrazol-1-yl)1-piperidinecarboxylate The title compound was prepared from the product of Preparation 5 with tert-butyl 4-[(methylsulfonyl)oxy]-1-piperidinecarboxylate (WO 93/19059) as alkylating agent, using the method of Preparation 19.

1H NMR (400 MHz, CDCl$_3$): δ=1.00 (t, 3H), 1.10 (t, 3H), 1.45 (s, 9H), 1.85–1.95 (m, 4H), 2.10 (m, 2H), 2.84 (m, 4H), 4.10–4.30 (m, 3H), 4.50 (t, 2H), 5.10 (s, 1H), 6.60 (s, 1H), 8.40 (s, 1H), 8.72 (s, 1H), 10.30 (s, 1H)

LRMS (TSP—positive ion) 628 (MH$^+$).

Anal. Found C, 47.55; H, 5.71; N, 13.07 Calcd for C$_{25}$H$_{35}$O$_5$N$_6$I.0.3H$_2$O, C, 47.52; H, 5.68; N, 13.30.

COMPARATIVE EXAMPLE A

Preparation of Compound 1A 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one

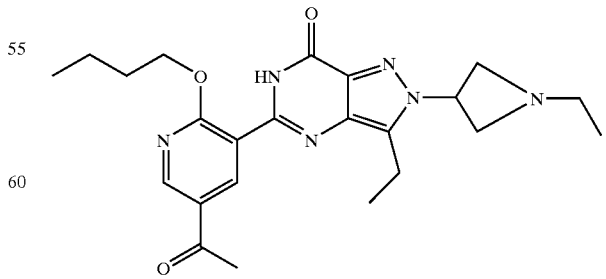

Preparation A(c)—5-Acetyl-N-[3-(aminocarbonyl)-5-ethyl-1H-pyrazol-4-yl]-2-ethoxynicotinamide

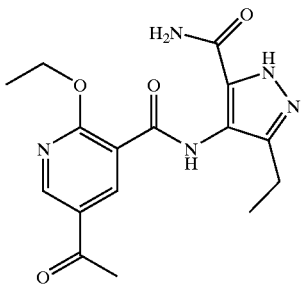

A solution of the title compound from Preparation 1(b) (5.70 g, 27.3 mmol) and O(7-azabenzotriazol-1-yl)-N,N,N',N'-tetramethyluronium hexafluor-phosphate (10.9 g, 28.6 mmol) in dichloromethane (100 mL) was added to a solution of 4-amino-3-ethyl-1H-pyrazole-5-carboxamide[1] (4.20 g, 27.3 mmol) and diisopropylethylamine (23.7 mL, 136.2 mmol) in dichloromethane (115 mL) under nitrogen. After 1 h the mixture was diluted with brine (100 mL) and washed with a saturated aqueous sodium bicarbonate solution (100 mL) and 2 N HCl (100 mL). Each aqueous layer was extracted with dichloromethane (100 mL), and the combined organics washed with brine (100 mL), dried ($MgSO_4$) and concentrated in vacuo. An analytical sample of the title compound was obtained by trituration with ethyl acetate, followed by recrystallisation from ethanol, while the remainder was purified by column chromatography on silica gel (eluting with 95:5 $CH_2Cl_2$:MeOH) to yield the title compound as a white solid (total weight=7.8 g, 22.5 mmol, 83%): mp 217–219° C; 1H NMR (400 MHz, DMSO-d): δ=1.10 (t, 3H, J=7.6 Hz), 1.42 (t, 3H, J=7.1 Hz), 2.56 (s, 3H), 2.73 (q, 2H, J=7.6 Hz), 4.62 (q, 2H, J=6.9 Hz), 7.26 (br s, 1H), 7.48 (br s, 1H), 8.71 (d, 1H, J=1.8 Hz), 8.91 (d, 1H, J=2.4 Hz), 10.52 (br s, 1H), 12.93 (br s, 1H); LRMS (m/z) ($TSP^+$) 346.2 ($MH^+$).

Preparation A(d)
tert-Butyl 3-[4-{[(5-acetyl-2-ethoxy-3-pyridinyl)carbonyl]amino}-3-(aminocarbonyl)-5-ethyl-1H-pyrazol-1-yl]-1-azetidinecarboxylate

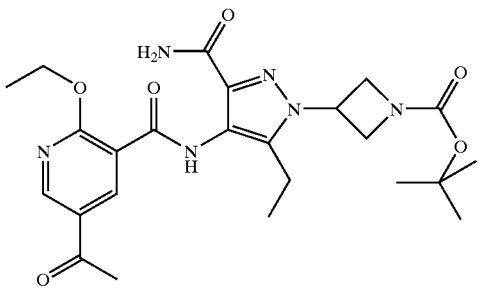

Cesium carbonate (46.4 g, 142 mmol) was added to a stirring solution of the title compound of Preparation A(c) (32.8 g, 95.0 mmol) and tert-butyl-3-iodo-1-azetidinecarboxylate (40.4 g, 143 mmol) in N,N-dimethylformamide (400 mL), and the reaction mixture was heated at 50° C. for 16 hours. The solvent was then removed in vacuo, and the residue triturated from ethyl acetate (100 mL). The resulting solid was filtered off, washed with ethyl acetate and partitioned between dichloromethane (500 mL) and water (300 mL) in the presence of concentrated hydrochloric acid (5 mL). The organic layer was separated, and the aqueous layer was extracted further with dichloromethane (2×100 mL). The combined organic layers were dried ($Na_2SO_4$) and concentrated in vacuo. The resulting crude product was triturated from acetonitrile, filtered and washed with acetonitrile and ether to yield the title compound as a white solid (30.3 g, 60.0 mmol, 63%): mp 220–223° C; 1H NMR (400 MHz, $CDCl_3$): δ=1.15 (t, 3H, J=7.6 Hz), 1.44 (s, 9H), 1.54 (t, 3H, J=7.1 Hz), 2.57 (s, 3H), 2.83 (q, 2H, J=7.3), 4.32 (t, 2H, J=8.1 Hz), 4.37–4.46 (m, 2H), 4.74 (q, 2H, J=7.1 Hz), 5.02–5.10 (m, 1H), 5.33 (br s, 1H), 6.72 (br s, 1H), 8.85 (d, 1H, J=2.5 Hz), 8.98 (d, 1H, J=2.4 Hz), 10.49 (br s, 1H); LRMS (m/z) ($ES^+$) 523.0 ($MNa^+$), ($ES^-$) 499.0 ($MH^-$).

Preparation A(e)
tert-Butyl 3-[5-(5-acetyl-2-butoxy-3-pyridinyl)-3-ethyl-7-oxo-6,7-dihydro-2H-pyrazolo[4.3-d]pyrimidin-2-yl]-1-azetidinecarboxylate

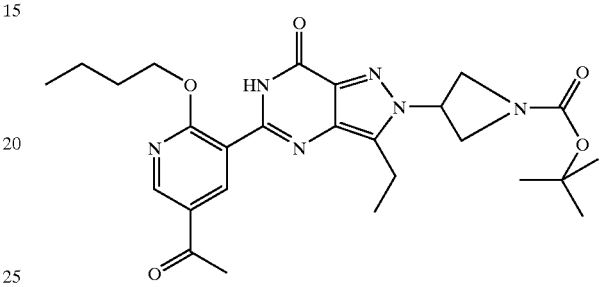

The title compound of Preparation A(d) (30.3 g, 60.0 mmol) and cesium carbonate (40.0 g, 123 mmol) were dissolved in n-butanol (500 mL) in the presence of 3 Å molecular sieves (5.00 g), and heated under reflux for 6 h. The first 90 mL of solvent were removed via distillation. The reaction mixture was then left at room temperature for 16 h, before being concentrated in vacuo. The residue was partitioned between ethyl acetate (400 mL) and water (400 mL), and solid carbon dioxide added until pH8. The organic layer was then separated, and the aqueous extracted further with ethyl acetate (400 mL). The combined organic layers were then dried ($Na_2SO_4$), and concentrated in vacuo. The crude product was purified by column chromatography on silica gel (eluting with $CH_2Cl_2$:MeOH:0.88$NH_3$ 98:2:0.2 to 96:4:0.4), followed by crystallisation from diisopropylether. This yielded the title compound, containing a 10% impurity, as white crystals (13.5 g, 26.4 mmol, 46%): mp 176–178° C.; 1H NMR (400 MHz, $CDCl_3$): δ=0.98 (t, 3H, J=7.6 Hz), 1.33 (t, 3H, J=7.6 Hz), 1.44 (s, 9H), 1.48–1.54 (m, 2H), 1.85–1.95 (m, 2H), 2.62 (s, 3H), 3.00 (q, 2H, J=7.6 Hz), 4.34 (t, 2H, J 6.8 Hz), 5.19–5.27 (m, 1H), 8.82 (d, 1H, J=2.4 Hz), 9.21 (d, 1H, J=2.4 Hz), 10.64 (br s, 1H); LRMS (m/z) ($ES^+$) 433 ($MNa^+$), ($ES^-$) 509 ($MH^-$).

Preparation A(f)
5-(5-Acetyl-2-butoxy-3-pyridinyl)-2-(3-azetidinyl)-3-ethyl-2,6-dihydro-7H-pyrazolo[4,3-d]pyrimidin-7-one

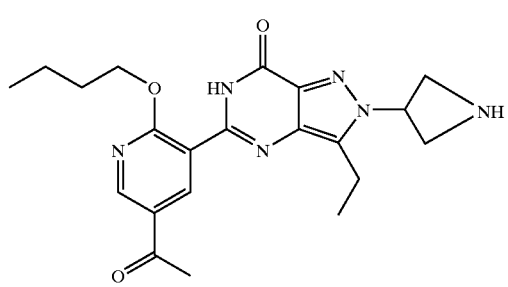

Trifluoroacetic acid (25 mL, 31% vol) was added to a solution of the title compound of Preparation A(e) (13.4 g, 262 mmol) in dichloromethane (80 mL) at 0° C., and the mixture was then stirred at room temperature for 1 hour. The reaction mixture was poured into toluene (100 mL) and concentrated in vacuo to yield an oil. The oil was azeotroped again with toluene (50 mL), and the residue taken up in isopropylacetate. The resulting precipitate was removed by filtration and dried in vacuo to yield the trifluoacetate salt of the title compound as a white solid (11.2 g, 17.5 mmol, 67%): 1H NMR (400 MHz, DMSO-d6): δ=0.87 (dt, 3H, J=1.5, 7.3 Hz), 1.19 (t, 3H, J=7.3 Hz), 1.35–1.44 (m, 2H), 1.63–1.72 (m, 2H), 2.58 (s, 3H), 2.92 (q,2H, J=7.8 Hz), 3.78 (t, 2H, J=7.6 Hz), 4.05–4.11 (m, 2H), 4.34–4.43 (m, 2H), 5.45–5.53 (m, 1H), 8.39 (d, 1H, J=1.5 Hz), 8.90 (d, 1H, J=1.5 Hz); LRMS (m/z) (ES$^+$) 411.0 (MH$^+$), (ES$^-$) 409.0 (MH$^-$).

Preparation A(a)

5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one Potassium carbonate (4.80 g, 34.7 mmol) and ethyl iodide (1.4 mL, 17.5 mmol) were added to a cloudy solution of the title compound from Preparation A(f) (11.1 g, 17.4 mmol) in acetonitrile (600 mL), and then the reaction mixture was heated to 45–50° C. for 2.5 h. The solvent was then removed in vacuo, and the residue dissolved in dichloromethane:methanol:ammonia 95:5:0.5 (50 mL). The resulting solution was filtered, and then purified by column chromatography on silica gel (eluting with CH$_2$Cl$_2$:MeOH:0.88NH$_3$ 95:5:0.5 to 92:8:1). The product was crystallised from diisopropylether to yield the title compound as white crystals (4.90 g, 11.2 mmol, 64%).

COMPARATIVE EXAMPLE B

Preparation of Compound 1A 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one

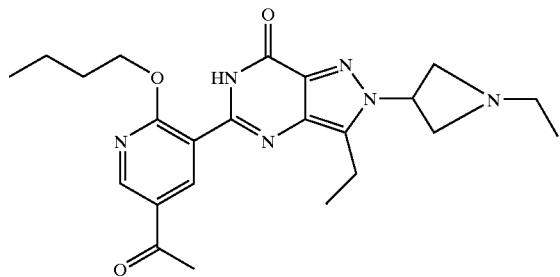

Cesium carbonate (38.6 g, 119 mmol) was added to a solution of the title compound from Preparation 2(e) (25.4 g, 59.3 mmol) in n-butanol (400 mL) In the presence of powdered 3A molecular sieves (10 g). The reaction mixture was then heated to reflux, and 20 mL of solvent removed via distillation into a splash trap. Refluxing was then continued for 4 h, after which the reaction mixture was cooled and filtered. The filtrate was concentrated In vacuo, and then purified by column chromatography on silica gel (eluting with CH$_2$Cl$_2$:MeOH:0.88NH$_3$ 95:5:0.5) to yield a green oil. The crude product was then purified by crystallisation from ethyl acetate, to yield the title compound as a white solid (9.00 g, 20.5 mmol, 35%): mp 143.0–144.0° C.; 1H NMR (400 MHz, DMSO-d$_6$): δ=1.01 (t, 3H, J=7.3 Hz), 1.03 (t, 3H, J=7.3 Hz), 1.37 (t, 3H, J=7.8 Hz), 1.49–1.59 (m, 2H), 1.89–1.97 (m, 2H), 2.65 (s, 3H), 2.66 (q, 2H, J=7.3 Hz), 3.03 (q, 2H, J=7.3 Hz), 3.72 (t, 2H, J=7.8 Hz), 3.90 (t, 2H, J=7.8 Hz), 4.68 (t, 2H, J=6.8 Hz), 5.12–5.19 (m, 1H), 8.85 (d, 1H, J=2.4 Hz), 9.23 (d, 1H, J=2.4 Hz), 10.62 (br s, 1H); LRMS (m/z) (TSP$^+$) 439.2 (MH$^+$); Anal. Found C, 63.00; H, 6.92; N, 19.14; Calcd for C$_{23}$H$_{30}$N$_6$O$_3$ C, 63.00; H, 6.90; N, 19.16.

EXAMPLE 1

Preparation of Compound 1A 5-(5-Acetyl-2butoxy-3-pyridinyl)-3ethyl-2-(1-ethyl-3-azetidinyl)-2,6-dihydro-7H-pyrazolo[4,3-d]pyrimidin-7-one

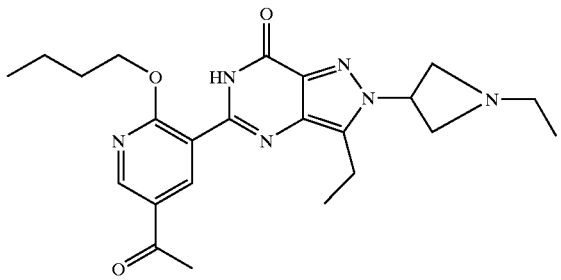

To a stirred suspension of 5-Acetyl-N-[3-(aminocarbonyl)-5-ethyl-1-(1-ethyl-3-azetidinyl)-1H-pyrazol-4-yl]-2-ethoxynicotinamide, the title compound of Preparation 2(e), (0.41 g, 0.96 mMol) in n-butanol (4 mL) under nitrogen atmosphere at room temperature was added n-butyl acetate (1.92 mMol, 0.25 mL) followed by potassium tert-butoxide (14.4 mMol, 162 mg) as a single solid portion. The reaction was left to stir at room temperature for 5 minutes before being heated to reflux overnight. The reaction was not complete so further n-butyl acetate (1.92 mMol, 0.25 mL) and potassium tert-butoxide (1.92 mMol, 215 mg) were added and the reaction was heated to reflux for a further 2 h. The reaction was allowed to cool to room temperature and then reduced to low volume (ca 1 mL) at reduced pressure. The crude concentrate was then diluted with DCM (50 mL) and washed with water (50 mL). The bi-phasic mixture was then passed through a pad of celite and the cake was washed with further DCM (50 mL). The two phases were then treated with brine (20 mL) and separated. The aqueous phase was then extracted with DCM (3×40 mL). The combined organics were then evaporated at reduced pressure to afford a dark brown oil that appeared to contain residual n-butanol. The crude residue was triturated with hexane (10 mL) and the resultant tan solid isolated by decanting the liquors to afford the title compound, 0.50 g, yield by HPLC=50%. M/Z=439 (M+H)$^+$.

EXAMPLE 2

Preparation of Compound 1A 5-(5-Acetyl-2-butoxy-3-pyridinyl)-3ethyl-2-(1-ethyl-3-azetidinyl)-2,6-dihydro-7H-pyrazolo[4,3-d]pyrimidin-7-one

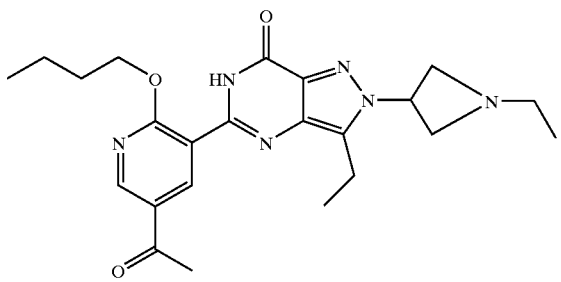

To a stirred suspension of 5-Acetyl-N-[3-(aminocarbonyl)-5-ethyl-1-(1-ethyl-3-azetidinyl)-1H-pyrazol-4-yl]-2-ethoxynicotinamide, the title compound of Preparation 2(e), (1.07 g, 2.5 mMol) in n-butanol (10 mL) under nitrogen atmosphere at room temperature was added n-butyl acetate (7.5 mMol, 0.87 mL) followed by potassium carbonate (7.5 mMol, 1.04 mg) as a single solid portion. The reaction was left to stir at room temperature for 5 minutes before being heated to reflux for 24 hours. The reaction was allowed to cool to room temperature and then reduced to low volume (ca 2 to 3 mL) at reduced pressure. The crude concentrate was then diluted with water (20 mL), this aqueous mixture was then treated with dilute HCl until pH 7 was attained at which point the remaining solvent was azeotroped out under reduced pressure. The resulting precipitate was cooled and filtered and the solid product dried to afford the title compound, 1.09 g, yield by HPLC=81%. M/Z=439 (M+H)$^+$.

Thus the process according to the present invention (i.e. using the hydroxide trapping agent), as illustrated hereinbefore by Examples 1 and 2 is a more efficient (2-steps from the coupling reaction) process for the preparation of compounds of general formula 1, and in particular compound 1A, compared to the process of Comparative Example A which requires 5 steps from the coupling reaction to furnish compounds of general formula 1. Further, the process of Examples 1 and 2 provides improved yields versus the process of comparative example A.

The process of the present invention as illustrated by Example 2 provides compound of general formula I, in particular compound 1A in of 81% from the compound of general formula III, specifically compound IIIA using the process of the present invention whilst Comparative Example B provides only 35% yield. In particular the coupling of compounds IXA and XIIA followed by cyclisation of compound IIIA to IA as exemplified herein in Example 2 provides the desired material in 56% yield whereas the corresponding reaction sequence in WO 01/27112 provides a yield of 35%.

Additionally, in accordance with the invention, the intermediate compounds (IX) (more particularly (IXA)) can be prepared from commercially available starting materials (2-chloro or 2-hydroxy nicotinic acid) in better yield than the corresponding reaction sequence in WO 01/27112.

More particularly compounds of general formula (IA) can be prepared in an overall yield of about 56% (from the corresponding intermediate compounds (IXA) and (XIIA)) according to the process of the present invention, as opposed to a yield of is about 10% via the process detailed in WO 01/27112 and yields of about 10% and about 24% versus Comparative Examples A and B. Furthermore, the reaction scheme of the present invention Is safer and cheaper to operate, and in the case of the process for the preparation of intermediates (IX)/(IXA) also involves less steps (and processing time).

In a preferred aspect compounds of formula (I) and (IA) are prepared from 2-hydroxy nicotinic acid or 2-chloro nicotinic acid in accordance with Schemes 1 and 2. In particular preparative example 1(b) illustrates an improved process for the preparation of compounds of general formula IXA from compounds of VIA in a yield of 63%.

Thus, in a preferred aspect of the invention there is provided a process for the preparation of a compound of formula (I) and (IA) according to the Scheme 4 as hereinbefore detailed.

Preliminary analysis indicates that compound 1A is anhydrous and non-hygroscopic which are desirable properties for compounds in the formulation of certain pharmaceutical products, such as, for example, tablets.

Differential Scanning Calorimetry (DSC) measurements were made for the compound 1A (of Example A). The sample was scanned at 20° C./minute, ambient to 300° C. on a T. A. Instruments Series 2910 machine and the flow gas was nitrogen. The DSC trace showed a sharp endotherm at 141° C. (ΔH 87.2 J/g), due to the material melting. Following this event the sample decomposed.

Powder X-Ray Diffraction (PXRD) Data was generated in respect of the compound 1A (of Example A). The PXRD data for was obtained from a sample of the solid mounted on a silicon wafer and rotated to reduce the effects of particle size and orientation. The solid sample was exposed to X-ray radiation using $CuK_{\alpha 1}$ (λ=1.5406 Å) and scanned through an angular range of 2° to 55° 2-Theta (θ) on a Siemens D5000 powder X-Ray diffractometer equipped with variable slits and a graphite secondary monochromator.

The main peaks of the resulting PXRD pattern are illustrated in Table 1.

TABLE 1

| 2-Theta (°) | Intensity (%) | 2-Theta (°) | Intensity (%) | 2-Theta (°) | Intensity (%) | 2-Theta (°) | Intensity (%) |
|---|---|---|---|---|---|---|---|
| 7.93 | 100 | 17.68 | 3.7 | 24.56 | 3.5 | 35.65 | 1.2 |
| 8.14 | 11.1 | 18.59 | 2.6 | 25.29 | 1.0 | 37.30 | 0.9 |
| 12.21 | 0.8 | 20.36 | 2.3 | 26.51 | 1.2 | 40.38 | 1.2 |
| 12.96 | 0.8 | 20.64 | 4.8 | 27.79 | 2.8 | 41.04 | 1.3 |
| 13.39 | 1.4 | 21.08 | 2.4 | 28.40 | 4.0 | 43.50 | 1.1 |
| 14.06 | 9.8 | 21.54 | 5.3 | 29.26 | 1.3 | 44.45 | 0.9 |
| 15.36 | 2.3 | 22.17 | 2.4 | 29.83 | 4.9 | 46.11 | 0.8 |
| 15.89 | 28.0 | 23.57 | 21.4 | 30.20 | 4.8 | 46.78 | 1.2 |
| 16.20 | 3.4 | 23.90 | 12.9 | 32.31 | 0.9 | 47.81 | 1.2 |
| 16.90 | 0.8 | 24.33 | 3.2 | 32.77 | 3.6 | 54.60 | 1.1 |

Thus the present invention provides 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one material having a PXRD pattern substantially as defined in Table 1 when measured according to the method described hereinbefore.

As will be appreciated by the skilled crystallographer, whilst the relative intensities of the various peaks within Table 1 may vary due to a number of factors such as for example orientation effects of crystals in the X-ray beam or the purity of the material being analysed or the degree of crystallinity of the sample, the peak positions will remain substantially as defined in Table 1 with small variations being possible due to the height of the sample in the X-ray beam as a result of the height of the powder bed for example.

The skilled crystallographer will also appreciate that measurements using a different wavelength will result in different shifts according to the Bragg equation—nλ=2d sin θ.

Such further PXRD patterns of 5-(5-Acetyl-2-butoxy-3-pyridinyl)-3-ethyl-2-(1-ethyl-3-azetidinyl)-2,6-dihydro-7H- pyrazolo[4,3-d]pyrimidin-7-one generated by use of alternative wavelengths are considered to be alternative representations of the PXRD pattern of the crystalline material of the present invention and as such are within the scope of the present invention.

The same compound, as defined by the XRD pattern described in Table 1, when made via alternative routes (as detailed in Examples section hereinbefore) can have a melting point in the range of from 138° C. to 149° C. (measured using a Perkin Elmer $DSC_7/TGA7$ at a heating rate of 20° C./minute).

Preliminary analysis indicates that the crystalline compound 1A as defined herein tends to exist In one polymorphic form. Monomorphic compounds are particularly desirable for pharmaceutical purposes.

EXAMPLE 3
3-ethyl-5-(5-iodo-2-propoxy-3-pyridinyl)-1,6-dihydro-7H-pyrazolo[4,3-d]pyrimidin-7-one A solution of the title compound from Preparation 5 (1.0 g, 2.3 mmol) in n-propanol (10 mL) and ethyl acetate (0.5 mL) was treated with potassium tert-butoxide (253 mg, 2.3 mmol) and heated to reflux for 24 h. After evaporation to dryness, the reaction mixture was partitioned between ethyl acetate and water whereupon a white solid precipitated which was separated by filtration. The organic phase was separated, dried over $Na_2SO_4$, concentrated and combined with the above solid, and this was then washed with ethyl acetate and recrystallised from hot methanol-dichloromethane to afford the title compound as a white solid (553 mg, 1.3 mmol).

$^1$H NMR (300 MHz, $d_6$-DMSO): δ=0.9 (t, 3H), 1.3 (t, 3H), 1.6–1.8 (m, 2H), 2.8–2.95 (br m, 2H), 4.25 (t, 2H), 8.25 (s, 1H), 8.5 (s, 1H).

LRMS (TSP) 426 ($MH^+$), 443 ($MNH_4^+$).

Analysis: found C, 42.40; H, 3.69; N, 16.39. Calcd for $C_{15}H_{16}IN_5O_2$: C, 42.37; H, 3.796; N, 16.47%.

EXAMPLE 4
5-[2-(Cyclobutyloxy)-5-nitro-3-pyridinyl]-1-methyl-3-propyl-1,6-dihydro-7H-pyrazolo[4,3-d]pyrimidin-7-one The title compound of Preparation 10 (1.0 g, 2.66 mmol), and potassium hexamethyldisilazide (1.72 g, 10.63 mmol) suspended in cyclobutanol (5 mL) and ethyl acetate (0.5 mL) was heated to reflux for 14 h. After cooling, the solvent was removed in vacuo and the residue taken up in water (20 mL) and extracted with dichloromethane (3×50 mL). Combined organic extracts were washed with brine (50 mL), dried over $MgSO_4$ and concentrated to a yellow solid (~800 mg). Purification by column chromatography (elution with 30:70 ethyl acetate:pentane) gave the title compound (295 mg, 0.76 mmol).

m.p. 212–4° C. 1H NMR (300 MHz, $CDCl_3$): δ=1.05 (t, 3H), 1.75–2.1 (m, 4H), 2.3–2.4 (m, 2H), 2.5–2.7 (m, 2H), 2.95 (t, 2H), 4.3 (s, 3H), 5.5–5.6 (m, 1H), 9.1 (s, 1H), 9.5 (s, 1H), 10.8 (br s, 1H).

LRMS (TSP) 385 ($MH^+$).

Analysis: Found C, 56.03; H, 5.28; N, 21.63. Calcd for $C_{18}H_{20}N_6O_4$: C, 56.24; H, 5.24; N, 21.86%.

EXAMPLE 5
3-Ethyl-5-(5-iodo-2-propoxy-3-pyridinyl)-1-[2-(4-morpholinyl)ethyl]-1,6-dihydro-7H-pyrazolo[4,3-d]pyrimidin-7-one The title compound of Preparation 13 (15.78 g, 28.4 mmol) was dissolved in n-propanol (200 mL), ethyl acetate (6 mL) and potassium t-butoxide (3.2 g, 28.4 mmol) were added and the resultant mixture heated to reflux for 6 h. Additional potassium t-butoxide (1.6 g, 14.2 mmol) was added and the mixture heated for a further 2 h, after which the solvent was removed in vacuo. The residue was partitioned between water (50 mL) and dichloromethane (100 mL) and the organic phase separated. The aqueous phase was extracted with dichloromethane (2×100 mL) and the combined organics dried over $MgSO_4$ and reduced to a yellow solid (~17 g). Purification by column chromatography (elution with ethyl acetate) gave the title compound (13.3 g, 24.1 mmol).

m.p. 175–177° C.

1H NMR (300 MHz, $CDCl_3$): δ=1.1 (t, 3H), 1.4 (t, 3H), 1.9–2.05 (m, 2H), 2.45–2.55 (m, 4H), 2.85 (t, 2H), 3.0 (q, 2H), 3.6–3.65 (m, 4H), 4.5 (t, 2H), 4.7 (t, 2H), 8.4 (s, 1H), 9.0 (s, 1H), 10.95 (br s, 1H).

LRMS (TSP) 540 ($MH^-$).

Analysis: found C, 46.79; H, 5.01; N, 15.44. Calcd for $C_{21}H_{27}N_6O_3I$: C, 46.85; H, 5.05; N, 15.61%.

EXAMPLE 6
4-{[5-(2-Ethoxy-5-iodo-3-pyridinyl)-3-ethyl-7-oxo-6,7-dihydro-2H-1-pyrazolo[4,3-d]pyrimidin-2-yl]methyl}benzonitrile The title compound was prepared from the title compound of Preparation 16 in ethanol using the method of example 3.

1H NMR (400 MHz, $CDCl_3$): δ=1.25 (t, 3H), 1.5 (t, 3H), 2.95 (q, 2H), 4.6 (q, 2H), 5.6 (s, 2H), 7.25 (d, 2H), 7.60 (d, 2H), 8.40 (d, 1H), 8.95 (d, 1H), 10.8 (br s, 1H).

LRMS 527 ($MH^+$), 549 ($MNa^+$).

EXAMPLE 7
5-(2-Propoxy-5-iodo-3-pyridinyl)-3-ethyl-2-(2-pyridinylmethyl)-2,6-dihydro-7H-pyrazolo[4,3d]pyrimidin-7-one The title compound was prepared from the product of Preparation 17 using the method of example 3.

m.p. 228.9–233.8° C.

1H NMR (400 MHz, $CDCl_3$): δ=1.05 (t, 3H), 1.25 (t, 3H), 1.90 (m, 2H), 3.00 (q, 2H), 4.50 (t, 2H), 5.65 (s, 2H), 7.05 (d, 1H), 7.20 (m, 1H), 7.60 (t, 1H), 8.40 (s, 1H), 8.55 (d, 1H), 8.95 (s, 1H), 10.70 (s, 1H).

LRMS (ES—positive ion) 517 ($MH^+$).

Anal. Found C, 48.73; H, 3.89; N, 16.14. Calcd for $C_{21}H_{21}O_2N_6I$: C, 48.85; H, 4.10; N, 16.28.

EXAMPLE 8
tert-Butyl 3-[3-ethyl-5-(5-iodo-2-propoxy-3-pyridinyl)-7-oxo-6,7-dihydro-2H-pyrazolo[4,3-d]pyrimidin-2-yl]-1-azetidinecarboxylate The title compound was prepared from the product of Preparation 19 using the method of example 3.

1H NMR (400 MHz, $CDCl_3$): δ=1.05 (t, 3H), 1.30 (t, 3H), 1.43 (s, 9H), 1.87–1.96 (m, 2H), 3.00 (q, 2H), 4.34 (t, 2H), 4.49 (t, 2H), 4.60 (br s, 2H), 5.20 (t, 1H), 8.41 (d, 1H), 8.94 (s, 1H), 10.75 (br s, 1H).

LRMS (TSP—positive ion) 598.1 ($MNH_4^+$).

Anal. Found C, 47.54; H, 5.02; N, 14.09 Calcd for $C_{23}H_{29}O_4N_6I$: C, 47.60; H, 5.04; N, 14.48.

EXAMPLE 9
tert-Butyl 4-[3-ethyl-5-(5-iodo-2-propoxy-3-pyridinyl)-7-oxo-6,7-dihydro-2H-pyrazolo[4,3-d]pyrimidin-2-yl]-1-piperidinecarboxylate The title compound was prepared from the product of Preparation 20 using the method of example 3.

1H NMR (400 MHz, $CDCl_3$): δ=1.10 (t, 3H), 1.40 (t, 3H), 1.45 (s, 9H), 1.92 (m, 4H), 2.40 (m, 2H), 2.90 (m, 2H), 3.08 (q, 2H), 4.38 (m, 3H), 4.50 (t, 2H), 8.40 (s, 1H), 8.98 (s, 1H), 10.69 (s, 1H).

EXAMPLE 10

3-Ethyl-1-[2-(4-morpholinyl)ethyl]-5-{2-propoxy-5-[(trimethylsilyl)ethynyl]-3-pyridinyl}-1,6-dihydro-7H-pyrazolo[4,3-d]pyrimidin-7-one Trimethylsilylacetylene (0.39 mL, 2.79 mmol) was added to a solution of the title compound of example 5 (1.0 g, 1.86 mmol) in triethylamine (20 mL). Acetonitrile (1 mL), bis(triphenylphosphine)palladium (II) chloride (33 mg, 2.5 mol %), and copper (I) iodide (9 mg, 2.5 mol %) were added and the resultant mixture stirred at room temperature for 1 h after which further trimethylsilylacetylene (0.39 mL, 2.79 mmol) was added and the mixture stirred for 10 h. After removal of the solvent in vacuo, the residue was partitioned between ethyl acetate (25 mL) and water (20 mL), the aqueous phase separated and extracted with further ethyl acetate (3×25 mL). Combined organics were washed with brine (25 mL), dried over $MgSO_4$, and concentrated to an oil which was crystallised from diisopropyl ether to afford the title compound as a white solid (156 mg, 0.30 mmol). The addition of pentane to the concentrated mother liquors afforded a second crop (509 mg, 1.0 mmol).

m.p. 132–134° C.

1H NMR (300 MHz, $CDCl_3$): δ=0.25 (s, 9H), 1.1 (t, 3H), 1.4 (t, 3H), 1.95–2.05 (m, 2H), 2.45–2.5 (m, 4H), 2.85 (t, 2H), 3.0 (q, 2H), 3.55–3.65 (m, 4H), 4.55 (t, 2H), 4.7 (t, 2H), 8.35 (s, 1H), 8.8 (s, 1H), 11 (br s, 1H).

LRMS (ES—negative ion) 507 (M–H)⁻. (ES—positive ion) 509 ($MH^+$).

Analysis: found C, 61.18; H, 7.12; N, 16.53. Calcd for $C_{26}H_{36}N_6O_3Si$ : C, 61.39; H, 7.13; N, 16.52%.

EXAMPLE 11

5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one hydrochloride A solution of 4M hydrochloric acid in dioxan (1 mL) was added to ethyl acetate (3 mL). An aliquot of this solution (0.3 mL), was then added to a solution of 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one (132 mg, 0.3 mmol) in ethyl acetate (5 mL) giving a precipitate. This mixture was warmed to 50° C. for 10 minutes, then allowed to cool to 0° C. The resulting powder was filtered, washed with ethyl acetate and dried at 50° C. in vacuo, to afford the title compound, 118 mg (81%).

m.p. 153–159° C.

¹Hnmr ($CDCl_3$, 300 MHz) δ 0.89 (t, 3H, J=7.3 Hz), 1.20 (m, 3H), 1.24 (t, 3H, J=7.7 Hz), 1.41 (m, 2H), 1.71 (m, 2H), 2.61 (s, 3H), 2.97 (m, 2H), 3.40 (m, 2H), 4.44 (t, 2H, J=6.2 Hz), 4.47 (m, 2H), 4.71 (m, 2H), 5.60 (m, 0.5H), 5.80 (m, 0.5H), 8.40 (d, 1H, J=2.3 Hz), 8.94 (d, 1H, J=2.3 Hz), 10.60 (bs, 1H), 11.20 (bs, 0.5H), 11.94 (s, 0.5H) (1:1 mixture of cis and trans isomers)

Microanalysis found: C, 56.89; H, 6.65; N, 17.29 $C_{23}H_{30}N_6O_3$;HCl requires C, 57.08; H, 6.66; N, 17.36%.

Powder X-Ray Diffraction (PXRD) Data was generated in respect of the compound of Example 11 in accordance with the method detailed hereinbefore for the compound of Example 1. The main peaks of the resulting PXRD pattern are illustrated in Table 2.

TABLE 2

| 2-Theta (°) | Intensity (%) | 2-Theta (°) | Intensity (%) | 2-Theta (°) | Intensity (%) | 2-Theta (°) | Intensity (%) |
|---|---|---|---|---|---|---|---|
| 6.40 | 44.1 | 15.42 | 30.9 | 23.14 | 38.6 | 28.16 | 46.4 |
| 7.71 | 50.8 | 17.20 | 34.4 | 23.78 | 47.6 | 29.13 | 37.9 |
| 10.26 | 14.8 | 18.28 | 29.6 | 25.33 | 47.1 | 32.61 | 28.1 |
| 10.81 | 32.2 | 18.97 | 23.8 | 26.14 | 89.4 | 35.21 | 23.2 |
| 12.25 | 13.8 | 21.28 | 28.9 | 26.52 | 100 | 36.41 | 28.1 |
| 12.87 | 17.7 | 21.88 | 41.8 | 27.51 | 53.6 | 45.77 | 20.9 |

Thus the present invention provides 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one hydrochloride material having a PXRD pattern substantially as defined in Table 2 when measured according to the method described hereinbefore.

EXAMPLE 12

5-(5-Acetyl-2-butoxy-3-pyridinyl)-3-ethyl-2-(1-ethyl-3-azetidinyl)-2,6dihydro-7H-pyrazolo[4,3-d]pyrimidin-7-one benzenesulfonate 5-(5-Acetyl-2-butoxy-3-pyridinyl)-3-ethyl-2-(1-ethyl-3-azetidinyl)-2,6-dihydro-7H-pyrazolo[4,3-d]pyrimidin-7-one (88 mg, 0.2 mmol) was dissolved in warm ethyl acetate (2 mL). A solution of benzenesulfonic acid (32 mg, 0.2 mmol) in ethyl acetate (2 ml) was then added, giving a precipitate. This mixture was warmed to 50° C. for 15 minutes, then allowed to cool to 0° C. The resulting solid was filtered, washed with ethyl acetate and dried in vacuo, to afford the title compound as a white solid 89 mg (74%).

m.p. 228–229° C.

¹Hnmr ($CDCl_3$, 300 MHz) δ 0.90 (t, 3H, J=7.3 Hz), 1.16–1.26 (m, 6H), 1.42 (m, 2H), 1.71 (m, 2H), 2.62 (s, 3H), 2.96 (m, 2H), 3.35 (m, 2H), 4.44 (t, 2H, J=6.6 Hz), 4.52 (m, 2H), 4.65 (m, 1H), 4.76 (m, 1H), 5.70 (m, 1H), 7.30 (m, 3H), 7.60 (m, 2H), 8.40 (d, 1H, J=2.2 Hz), 8.95 (d, 1H, J=2.2 Hz), 9.80 (bs, 0.5H), 10.25 (bs, 0.5H), 11.95 (s, 1H) (1:1 mixture of cis and trans isomers)

Microanalysis found: C, 57.56; H, 5.98; N, 13.74. $C_{23}H_{30}N_6O_3$;$C_6H_6O_3S$;$0.5H_2O$ requires C, 57.51; H, 6.16; N, 13.87%.

The compound of Example 12 was found to be non-hygroscopic which is for compounds in the formulation of certain pharmaceutical products, such as, for example, tablets.

Dynamic Vapour Sorption (DVS) measurements were made for the compound of Example 12 by exposing a solid sample to controlled relative humidity (% RH) and weight change recorded with time on an automated water sorption analyser. The sorption/desorption isotherm for the compound of Example 12 shows that on drying the material lost a small amount of weight (0.9%) due to loss of residual solvent or surface moisture.

Powder X-Ray Diffraction (PXRD) Data was generated in respect of the compound of Example 13 in accordance with the method detailed hereinbefore for the compound of Example 1. The main peaks (those over 10% intensity) of the resulting PXRD pattern are illustrated in Table 3.

TABLE 3

| 2-Theta (°) | Intensity (%) | 2-Theta (°) | Intensity (%) | 2-Theta (°) | Intensity (%) |
|---|---|---|---|---|---|
| 3.80 | 81.8 | 18.46 | 10.6 | 24.48 | 35.3 |
| 7.79 | 90.6 | 18.77 | 45.4 | 24.88 | 15.6 |
| 8.66 | 14.4 | 20.66 | 16.8 | 25.92 | 22.6 |
| 10.83 | 14.6 | 20.91 | 36.7 | 26.64 | 20.7 |
| 11.36 | 11.9 | 21.70 | 37.7 | 27.00 | 12.4 |
| 13.72 | 11.1 | 21.97 | 52.8 | 27.33 | 15.1 |
| 15.16 | 23.1 | 22.21 | 21.5 | 27.56 | 14.9 |
| 16.03 | 19.7 | 22.82 | 31.5 | 27.95 | 11.1 |
| 16.67 | 13.2 | 23.28 | 16.0 | 31.62 | 15 |
| 17.26 | 18.7 | 23.60 | 100.0 | 33.06 | 10.9 |
| 17.56 | 11.1 | 24.05 | 35.5 | 41.56 | 11.6 |
|  |  |  |  | 48.20 | 11.4 | thus the present invention provides 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one benzenesulfonate material having a PXRD pattern substantially as defined in table 3 when measured according to the method described hereinbefore.

What is claimed is:

1. A process for the preparation of a compound of general formula (I):

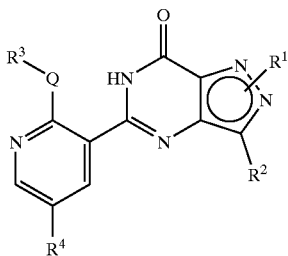

or a pharmaceutically or veterinarily acceptable salt, polymorph and/or solvate thereof, wherein Q represents O or $NR^5$ $R^1$ represents H, lower alkyl, Het, alkylHet, aryl or alkylaryl (which latter five groups are all optionally substituted with one or more substituents selected from cyano, nitro, lower alkyl, $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

$R^2$ represents H, cyano, nitro, $OR^6$, $OC(O)R^7$, $C(O)R^8$, $C(O)OR^9$, $C(O)NR^{10}R^{11}$, $NR^{12}R^{13}$, $SO_2NR^{14}R^{15}$, lower alkyl, Het, alkylHet, aryl or alkylaryl (which latter live groups are all optionally substituted with one or more substituents selected from cyano, nitro, lower alkyl, $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

$R^3$ represents H, lower alkyl, alkylHet or alkylaryl (which latter three groups are all optionally substituted with one or more substituents selected from cyano, nitro, lower alkyl, $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

$R^4$ represents H, halo, cyano, nitro, $OR^6$, $C(O)R^8$, $C(O)OR^9$, $C(O)NR^{10}R^{11}$, $NR^{10}R^{13}$, $NR^{16}Y(O)R^{17}$, $N[Y(O)R^{17}]_2$, $S(O)R^{18}$, $SO_2R^{19}$, $C(O)AZ$, lower alkyl, lower alkenyl, lower alkynyl, Het, alkylHet, aryl, alkylaryl (which latter seven groups are all optionally substituted with one or more substituents selected from cyano, nitro, lower alkyl, $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

Y represents C or S(O)

A represents lower alkylene

Z represents $OR^6$, Het or aryl (which latter two groups are both optionally substituted with one or more substituents selected from cyano, nitro, lower alkyl, $OR^6$, $OC(O)R^7$, $C(O)R^8$, $C(O)OR^9$, $C(O)NR^{10}R^{11}$, $NR^{12}R^{13}$ and $SO_2NR^{14}R^{15}$)

$R^{10}$ and $R^{11}$ independently represent H or lower alkyl (which latter group is optionally substituted with one or more substituents selected from cyano, nitro, lower alkyl, $OR^6$, $OC(O)R^7$, $C(O)R^8$, $C(O)OR^9$, $C(O)NR^{10a}R^{11a}$, $NR^{12}R^{13}$, $SO_2NR^{14}R^{15}$ and $NR^{20}S(O)_2R^{21}$ or Het or aryl optionally substituted with one or more of said latter thirteen groups) or one of $R^{10}$ and $R^{11}$ may be lower alkoxy, amino or Het, which latter two groups are both optionally substituted with lower alkyl $R^{10a}$ and $R^{11a}$ independently represent H or lower alkyl (which latter group is optionally substituted with one or more substituents selected from cyano, nitro, lower alkyl, $OR^6$, $OC(O)R^7$, $C(O)R^8$, $C(O)OR^9$, $SO_2NR^{14}R^{15}$ and $NR^{20}S(O)_2R^{21}$ or Het or aryl optionally substituted with one or more of said latter thirteen groups) or one of $R^{10a}$ and $R^{11a}$ may be lower alkoxy, amino or Het, which latter two groups are both optionally substituted with lower alkyl $R^{12}$ and $R^{13}$ independently represent H or lower alkyl (which latter group is optionally substituted with one or more substituents selected from $OR^6$, $C(O)OR^9$, $C(O)NR^{22}R^{23}$ and $NR^{24}R^{25}$), one of $R^{12}$ or $R^{13}$ may be C(O)-lower alkyl or C(O)Het (in which Het is optionally substituted with lower alkyl), or $R^{12}$ and $R^{13}$ together represent $C_{3-7}$ alkylene (which alkylene group is optionally unsaturated, optionally substituted by one or more lower alkyl groups and/or optionally interrupted by O or $NR^{26}$)

$R^{14}$ and $R^{15}$ independently represent H or lower alkyl or $R^{14}$ and $R^{15}$, together with the nitrogen atom to which they are bound, form a heterocyclic ring $R^{16}$ and $R^{17}$ independently represent H or lower alkyl (which latter group is optionally substituted with one or more substituents selected from $OR^6$, $C(O)OR^9$, $C(O)NR^{22}R^{23}$ and $NR^{24}R^{25}$) or one of $R^{16}$ and $R^{17}$ may be Het or aryl, which latter two groups are both optionally substituted with lower alkyl $R^5$, $R^6$, $R^7$, $R^8$, $R^9$, $R^{18}$, $R^{19}$, $R^{20}$, $R^{22}$, $R^{23}$, $R^{24}$ and $R^{25}$ independently represent H or lower alkyl $R^{18}$ and $R^{19}$ independently represent lower alkyl $R^{21}$ represents lower alkyl or aryl $R^{26}$ represents H, lower alkyl, aryl, $C(O)R^{27}$ or $S(O)_2R^{28}$ $R^{27}$ represents H, lower alkyl or aryl $R^{28}$ represents lower alkyl or aryl Het represents a four- to twelve-membered heterocyclic group, optionally substituted by one or more substituents selected from cyano, nitro, oxo, lower alkyl, $OR^6$, $OC(O)R^7$, $C(O)R_8$, $C(O)OR^9$, and $SO_2NR^{14}R^{15}$, which group contains one or more heteroatoms selected from nitrogen, oxygen, sulphur and mixtures thereof said process comprising reacting, in an inert, alcoholic, or mixed inert/alcohol solvent, a compound of formula (III), (IV) or (V) in the presence of $^-OR^3$ and a hydroxide trapping agent which is an ester of the formula

TOC(O)W wherein OT is $OR^3$ or OT is the residue of non-nucleophilic alcohol or TOH is an alcohol which can be azeotropically removed during the reaction;

and C(O)W is the residue of a carboxylic acid;

or, alternatively, in the case of compounds of formulae (IV) or (V) reacting, in an inert, alcoholic, or mixed inert/alcohol solvent and in the presence of an auxiliary base and a hydroxide trapping agent which is an ester of the formula

TOC(O)W as defined above

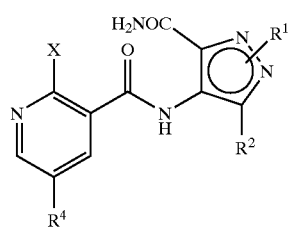
(III)

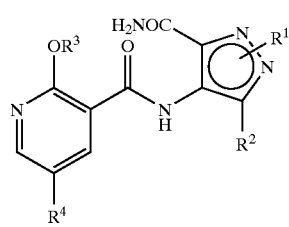
(IV)

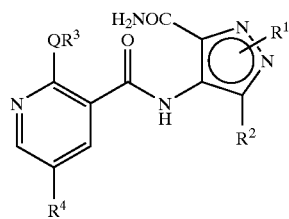
(V)

wherein X is a leaving group and Q and $R^1$ to $R^4$ are as defined above, provided that in said process, Q is not $NR^5$ when a compound of formula (III) or (IV) is used therein.

2. A process for the preparation of a compound of formula (IA):

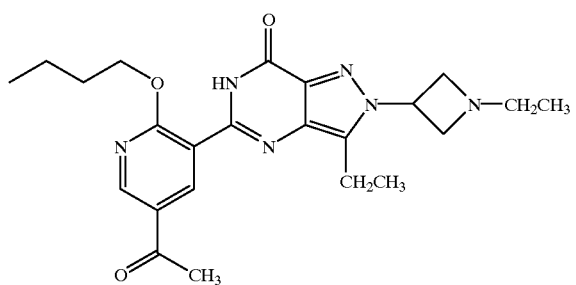
(IA)

said process comprising reacting a compound of formula (IIIA) or (IVA) respectively

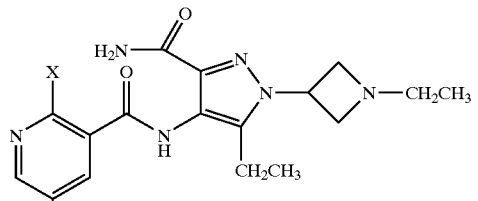
(IIIA)

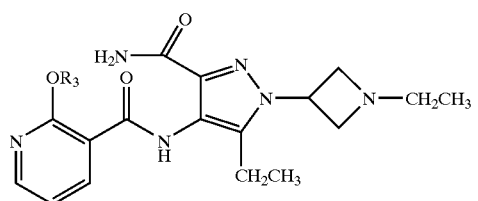
(IVA)

in the presence of $^-OR^3$ and a hydroxide trapping agent, which is an ester of the formula

TOC(O)W wherein OT is $OR^3$ or OT is a the residue of non-nucleophilic alcohol or TOH is an alcohol which can be azeotropically removed during the reaction;

and C(O)W is the residue of a carboxylic acid;

wherein $OR^3$ is $CH_3(CH_2)_3O$—, or alternatively in the case of compounds of formula (IVA) reacting in the presence of a hydroxide trapping agent and an auxiliary base, wherein $OR^3$ in the case of formation of compound (IA) from (IVA) is $CH_3(CH_2)_3O$— and wherein X in formulae (IIIA) is a leaving group.

3. A process according to claim 2 which comprises reacting a compound of formula (IIIA) wherein X is ethoxy in the presence of n-butyl acetate and potassium carbonate in n-butanol.

* * * * *